United States Patent [19]

Babcock et al.

[11] Patent Number: 5,332,582

[45] Date of Patent: * Jul. 26, 1994

[54] STABILIZATION OF AMINOSTEROIDS FOR TOPICAL OPHTHALMIC AND OTHER APPLICATIONS

[75] Inventors: John C. Babcock, Olga, Wash.; Jon R. Polansky, Mill Valley, Calif.; Lyle M. Bowman, Pleasanton, Calif.; Sheng-Wan Tsao, San Carlos, Calif.; Erwin C. Si, Alameda, Calif.; Santosh K. Chandrasekaran, Moraga, Calif.

[73] Assignee: Insite Vision Incorporated, Alameda, Calif.

[*] Notice: The portion of the term of this patent subsequent to Jun. 23, 2009 has been disclaimed.

[21] Appl. No.: 984,445

[22] Filed: Dec. 2, 1992

Related U.S. Application Data

[60] Continuation-in-part of Ser. No. 933,574, Aug. 24, 1992, Pat. No. 5,209,926, which is a continuation of Ser. No. 838,875, Feb. 19, 1992, abandoned, which is a division of Ser. No. 537,062, Jun. 12, 1990, Pat. No. 5,124,154.

[51] Int. Cl.$^5$ .............. A61K 47/28; A61K 31/59; A61K 37/22; A61K 37/52
[52] U.S. Cl. .............. 424/78.04; 424/78.02; 424/78.05; 424/78.06; 424/78.07; 424/423; 424/427; 424/428; 424/430; 424/434; 424/435; 424/436; 424/443; 424/450; 514/169; 514/170; 514/172; 514/176; 514/774; 514/777; 514/781; 514/785; 514/801; 514/887; 514/912; 514/913
[58] Field of Search .............. 424/78.04, 427, 428, 424/450, 434, 435, 436, 430, 423, 78.02, 78.05, 78.06, 78.07, 443; 514/169, 170, 172, 176, 774, 777, 781, 784, 785, 801, 912, 944, 887, 913

[56] References Cited

U.S. PATENT DOCUMENTS

| | | | |
|---|---|---|---|
| 2,798,053 | 7/1957 | Brown | 521/138 |
| 3,459,731 | 8/1969 | Gramera et al. | 536/103 |
| 3,947,573 | 3/1976 | Rankin | 514/397 |
| 4,039,662 | 8/1977 | Hecht et al. | 514/59 |
| 4,127,674 | 11/1978 | Leopold | 514/166 |
| 4,131,648 | 12/1978 | Choi et al. | 424/484 |
| 4,136,250 | 1/1979 | Mueller et al. | 528/29 |
| 4,192,827 | 3/1980 | Mueller et al. | 525/123 |
| 4,230,724 | 10/1980 | Cooper et al. | 514/570 |
| 4,271,143 | 6/1981 | Schoenwal et al. | 514/9 |
| 4,383,992 | 5/1984 | Lipari | 514/912 |
| 4,407,791 | 10/1983 | Stark | 424/78.04 |
| 4,407,792 | 10/1983 | Schoenwald et al. | 514/397 |
| 4,443,432 | 4/1984 | Garabedian et al. | 424/606 |
| 4,461,904 | 7/1984 | York, Jr. | 548/333.1 |
| 4,474,751 | 10/1984 | Haslam et al. | 514/11 |
| 4,478,818 | 10/1984 | Shell | 424/426 |
| 4,524,063 | 6/1985 | Wheeler | 514/555 |
| 4,548,990 | 10/1985 | Mueller et al. | 525/123 |
| 4,559,343 | 12/1985 | Han et al. | 514/264 |
| 4,596,795 | 6/1986 | Pitha | 514/58 |
| 4,615,697 | 10/1986 | Robinson | 424/428 |
| 4,617,186 | 10/1986 | Schefer et al. | 424/78.04 |
| 4,644,007 | 2/1987 | York, Jr. | 514/392 |
| 4,668,626 | 5/1987 | Kobayashi et al. | 435/95 |
| 4,686,214 | 8/1987 | Boltralik | 514/179 |
| 4,717,725 | 1/1988 | York, Jr. et al. | 514/278 |
| 4,727,064 | 2/1988 | Pitha | 514/58 |
| 4,737,492 | 4/1988 | Gerson et al. | 514/204 |
| 4,764,604 | 8/1988 | Muller | 536/103 |
| 4,820,737 | 4/1989 | Schoenwald et al. | 514/654 |
| 4,822,819 | 4/1989 | De Santis et al. | 514/530 |
| 4,911,920 | 3/1990 | Jani et al. | 424/78.04 |
| 4,983,586 | 1/1991 | Bodor | 514/912 |
| 5,002,935 | 3/1991 | Bodor | 514/912 |
| 5,017,566 | 5/1991 | Bodor | 514/912 |
| 5,024,998 | 6/1991 | Bodor | 514/912 |
| 5,099,019 | 3/1992 | McCall et al. | 544/295 |
| 5,120,843 | 5/1992 | McCall et al. | 544/123 |
| 5,124,154 | 6/1992 | Babcock | 424/427 |

FOREIGN PATENT DOCUMENTS

| | | |
|---|---|---|
| 81924 | 6/1983 | European Pat. Off. . |
| 0197571 | 10/1986 | European Pat. Off. . |
| 61-070996 | 4/1986 | Japan . |
| 61-197602 | 9/1986 | Japan . |
| 61-236802 | 10/1986 | Japan . |
| 62-003795 | 1/1987 | Japan . |
| 61-287902 | 1/1987 | Japan . |
| 62-106901 | 5/1987 | Japan . |
| 62-164701 | 7/1987 | Japan . |
| 62-281855 | 12/1987 | Japan . |
| 63-027440 | 2/1988 | Japan . |
| 63-036793 | 2/1988 | Japan . |
| 63-135402 | 6/1988 | Japan . |

(List continued on next page.)

OTHER PUBLICATIONS

Braughler et al., Biochemical Pharmacology, 37:3853–3860 (1988).

Irie et al., Pharmaceutical Research, vol. 5, No. 11, 1988, 713–717.

Kohler, Thrombosis Res., 9, 67 (1976).

Koizumi et al., Chem. Pharm. Bull., 35(8), 3413–3418 (1987).

Loftsson et al., Acta Pharm. Nord., 1(4), 185–193 (1989).

(List continued on next page.)

Primary Examiner—Paul R. Michl
Assistant Examiner—Carlos Azpuru
Attorney, Agent, or Firm—Howrey & Simon

[57] ABSTRACT

The invention provides methods for stabilizing aminosubstituted steroid therapeutic agents in topical ophthalmic and other pharmaceutical formulations using effective stabilizing amounts of lightly cross-linked carboxy-containing polymers. Stabilized and stabilized/solubilized pharmaceutical compositions adapted for various routes of administration are also described.

36 Claims, No Drawings

FOREIGN PATENT DOCUMENTS

| | | |
|---|---|---|
| 137542 | 9/1967 | New Zealand . |
| 153024 | 12/1970 | New Zealand . |
| 152836 | 4/1971 | New Zealand . |
| 159657 | 3/1972 | New Zealand . |
| 186631 | 5/1980 | New Zealand . |
| 190007 | 9/1980 | New Zealand . |
| 200475 | 8/1985 | New Zealand . |
| 215587 | 8/1989 | New Zealand . |
| 224288 | 12/1989 | New Zealand . |
| 222103 | 8/1990 | New Zealand . |
| 226433 | 6/1991 | New Zealand . |
| 231086 | 7/1991 | New Zealand . |
| 229649 | 12/1991 | New Zealand . |
| WO83/03544 | 10/1983 | PCT Int'l Appl. . |
| WO84/04680 | 12/1984 | PCT Int'l Appl. . |
| WO84/04681 | 12/1984 | PCT Int'l Appl. . |
| WO85/02767 | 7/1985 | PCT Int'l Appl. . |
| WO87/01706 | 3/1987 | PCT Int'l Appl. . |
| WO87/01943 | 4/1987 | PCT Int'l Appl. . |
| WO88/08424 | 11/1988 | PCT Int'l Appl. . |
| WO89/06964 | 8/1989 | PCT Int'l Appl. . |
| WO92/00044 | 1/1992 | PCT Int'l Appl. . |
| 2012634 | 4/1990 | Spain . |
| 0997682 | 2/1983 | U.S.S.R. . |
| 2007091 | 5/1979 | United Kingdom . |
| 2013084 | 9/1979 | United Kingdom . |

OTHER PUBLICATIONS

Okada et al., Chem. Pharm. Bull., 36(6), 2176-2185 (1988).

Pagington, Chemistry in Britain, May 1987, 455-458.

Pitha et al., Controlled Drug Delivery, Ed. S. D. Bruck, vol. I, CRC Press, Boca Raton, Fla., 125-148 (1983).

Pitha et al., International Journal of Pharmaceutics, 29, 73-82 (1986).

Inhibition of Diquant-Induced Lipid Peroxidation and Toxicity In Vivo by Novel Antioxidants, G. H. I. Wolfgang et al., The Toxicologist, Abstracts of the 29th Annual Meeting, vol. 10, No. 1, Feb. 1990.

Pitha et al., J. Pharm. Sci., vol. 74, No. 9, Sep. 1985, 987-990.

Pryor, Methods of Enzymology, 105, 293 (1984).

Snider et al., Int. J. Pharm., 66, 63-70 (1990).

Thorsteinn Loftsson, Pharm. Ztg Wiss., 4/136:5-10 (1991).

Uekama et al., CRC Critical Reviews in Therapeutic Drug Carrier Systems, vol. 3(1), 1-40 (1987).

Uekama, Topics in Pharmaceutical Sciences, 1987, eds. D. D. Breimer and P. Speiser, Elsevier Science Publishers B.V. (Biomedical Division), 1987, 181-194.

Yamamoto et al., International Journal of Pharmaceutics, 49, 163-171 (1989).

Yoshida et al., International Journal of Pharmaceutics, 46, 1988, 217-222.

U78517F, "A Second Generation Lazaroid with Potent Anti-Oxidant and Cerebro-Protective Activity in Models of CNS Injury and Ischemia", E. D. Hall et al., Journal of Neurotrauma, vol. 6, No. 3, Fall 1989, pp. 213-214.

"Inhibition of Carbon Tetrachlorid-Induced Lipid Peroxidation in Rat Hepatic Micro-somes-Dissociation from Hepatoprotective Effects In Vivo", T. W. Petry et al., Abstracts of the 4th International Symposium on Biological Reactive Intermediates, Jan. 14-17, 1990, Hosted by The Center for Toxicology, The University of Arizona, Tuscon, Ariz.

"Effects of the Antioxidants U74006F, U78517G and N,N-Diphenyl-p-phenylenediamine on Carbon Tetrachloride-Induced Toxicity in Precision-Cut Rat Lever Slices", G. H. I. Wolfgang et al., Abstracts of the 4th International Symposium on Biological Reactive Intermediates, Jan. 14-17, Hosted by The Center for Toxicology, The University of Arizona, Tucson, Ariz.

"Modulation of Diquat-Induced Toxicity in Vivo by Novel Inhibitors of Lipid Peroxidation and the Oxidant Diphenyl-p-Phenylenediamine", R. A. Jolly et al., The Toxicologist, Abstracts of the 29th Annual Meeting, vol. 10, No. 1, Feb. 1990.

Pharmaceutica Acta Helvetiae, vol. 39, pp. 546 et seq. (1964).

Pharmaceutical Acta Helvetiae, vol. 39, pp. 615 et seq. (1964).

Canadian Journal of Pharmaceutical Sciences, vol. 10, No. 1, pp. 16 et seq. (1975).

Klin. Mbl. Augenheilk. 189 (1986) at pp. 51-54 and pp. 254-257, Marquardt Opthalmology, "Gel Tears", Oct. 1984, vol. 91, No. 10, pp. 1199-1204, Liebowitz et al.

STABILIZATION OF AMINOSTEROIDS FOR TOPICAL OPHTHALMIC AND OTHER APPLICATIONS

This application is a continuation-in-part of application Ser. No. 07/933,574 filed Aug.24, 1992, now U.S. Pat. No. 5,209,926, as a file wrapper continuation of application Ser. No. 07/838,875, filed Feb. 19, 1992, now abandoned, which is itself a divisional of application Ser. No. 07/537,062, filed Jun.12, 1990, now U.S. Pat. No. 5,124,154. The entire disclosures of said prior applications are incorporated by reference herein and relied upon.

FIELD OF THE INVENTION

The present invention relates to methods for stabilizing amino-substituted steroid therapeutic agents in topical ophthalmic and other pharmaceutical formulations using lightly cross-linked carboxy-containing polymers. The invention further relates to topical ophthalmic and other pharmaceutical compositions comprising amino-substituted steroid therapeutic agents and lightly cross-linked carboxy-containing polymers.

BACKGROUND

It is known that oxygen-derived radical species are important mediators of several forms of tissue damage, such as ischemic and traumatic injuries to organs and tissues, inflammatory responses and injuries which result from the intra-cellular metabolism of chemicals and drugs. In particular, oxygen-derived radical species have been suggested as destructive forces in such maladies as head and spinal cord injury, stroke, shock, Parkinsonism, muscular dystrophy, emphysema, ARDS (acute respiratory distress syndrome), asthma, aging, post-myocardial infarct tissue destruction, drug toxicity, radiation damage, transplant rejection and burn damage.

In addition to their adverse effects on various other body tissues, oxidation reactions can also cause damage to the eye. It is known, for example, that the aqueous humor of the eye is rich in hydrogen peroxide and that the anterior tissues bathed by the aqueous humor exist in an extraordinarily oxidalive environment. It is further known that prolonged exposure of the eye to light of certain wavelengths can cause harm to anterior, posterior and other tissues of the eye. Indeed, prolonged exposure to light produces oxidative damage in many tissues such as the lens, retina and retinal pigmented epithelium. Additionally, chronic exposure to light and to an oxidative environment is believed to induce cumulative damage, which, depending on the severity of the exposure and the susceptibilies of the individual exposed can result, in the best of cases, in normal aging and discomfort and, in the worst of cases, in pathological disorders and loss of vision.

In addition to light exposure, such a cascade leading to the production of harmful oxidative species is initiated by inflammation, by trauma, by ischemia, by hemorrhaging by stimulation by a variety of drugs and endogenous cell regulators, by pressure exertion on tissues as occurs diurnally as a result of intraocular pressure changes in the anterior chamber of the eye, and indeed by a host of processes both normal and abnormal that occur continuously in the eye. Polyunsaturated fatty acids are also readily subjected to chemical (non-enzymatic) oxidation to yield hydroperoxides, hydroxy fatty acids and malondialdehyde, materials which can contribute to the overall damage that accumulates with time.

Thus, oxidative processes are now known to a play a role in age-related cataracts, light-induced retinal damage, other retinopathies such as diabetic retinopathy and age-related macular degeneration, inflammatory damage (such as that seen in uveitis), vascular leakage and edema (as in cystoid macular edema), accidental or surgical trauma, angiogenesis, corneal opacities, retrolental fibroplasia and some aspects of glaucoma.

To counteract the harmful effects of the oxidative processes described above, the body naturally produces a number of defensive compounds such as α-tocopherol (vitamin E, which is an antioxidant), ascorbic acid, glutathione, catalase and superoxide dismutase. Thus, vitamin E, is known to be a scavenger of both lipid peroxyl radicals and oxygen radicals, as well as to have a membrane-stabilizing action. Indeed, it is believed that chronic dietary vitamin E supplementation can attenuate postischemic cerebral (hypoperfusion) by inhibiting the lipid peroxidative process.

In order to enhance the eye's ability to protect from damaging oxidative processes such as can occur with aging or due to a sudden trauma, it has been proposed to supply vitamin E to the eye by oral administration in view of its known ability to inhibit oxidative processes. Vitamin E does scavenge free radicals and function as an antioxidant. However, it must be given chronically to have any effect. Moreover, even when administered chronically with other antioxidants, such as glutathione and vitamin C, the results are at best mixed.

A group of 21-aminosteroids has been found to act as antioxidants, and some aminosteroids have been employed intravenously, intraperitoneally and orally in the treatment of central nervous system injury, head and spinal injury, and edema associated with acute stroke. It has been reported that intravenous administration of a citrate buffered saline solution of 0.15% by weight of U-74600F for treatment of spinal cord or brain injury has been effective to arrest lipid peroxidation therein., It is also known that in performing toxicology studies with various drugs, polysorbate 80 and hydroxypropylcellulose and the like can be used as suspending agents in low viscosity formulations.

International Publication No. WO 87/01706, published Mar. 26, 1987, which discloses a number of aminosteroids and their therapeutic use in a variety of contexts, as well as administration techniques and dosages, does not disclose treatment or prevention of ophthalmic diseases or disorders. Nor does it disclose topical application to the eye or administration by intraocular injection. Moreover, prior art formulations which cannot be comfortably and effectively applied to the eye have limited applicability.

Applicants' great grandparent application Ser. No. 07/537,062, now U.S. Pat. No. 5,124,154, discloses methods and compositions which are designed to enhance the ability of the tissues of the eye to respond to trauma, to aging, to surgery, to the threat of glaucoma by increasing intraocular pressure, to the potential loss of vision from progression of macular degeneration and the like by supplementing, both acutely and chronically, the natural ability of the eye to resist oxidative damage. In one aspect, the '154 invention discloses methods of arresting processes (particularly oxidation processes) causing damage to the eye of a human or other animal that is subject to intraocular damage (particularly oxidative intraocular damage) and in need of improved visual function or prevention of its loss from such damage, wherein certain amino-substituted steroids which function as a therapeutic agent (particularly an antioxidant agent) are administered in an inert vehicle to the eye tissue by intraocular injection or topically. In another aspect, the '154 invention discloses methods of preventing or treating ophthalmic diseases or disorders in a human or other animal that is subject to intraocular damage (particularly oxidative intraocular damage) and in need of improved visual function or prevention of its loss from such damage, wherein an ophthalmically effective amount of certain amino-substituted steroids which function as a therapeutic agent (particularly an antioxidant agent) is administered, in an inert vehicle, to arrest presses (particularly oxidation processes) damaging to the eye. Compositions useful in the disclosed methods are also described.

The aminosteroids disclosed in International Publication No. WO 87/01706 and great grandparent U.S. Ser. No. 07/537,062 (now U.S. Pat. No. 5,124,154), as well as in parent Ser. No. 07/933,574, thus are valuable therapeutic agents, particularly as a consequence of their antioxidant activity. However, the aminosteroids suffer from stability problems and they can cause irritation. Moreover, because they are potent antioxidants, the aminosteroids are especially sensitive to oxidative degradation; moreover, these compounds are subject to hydrolytic degradation and rearrangement. Such instability can severely limit the usefulness of pharmaceutical compositions containing the aminosteroids, for example, by drastically shortening the shelf-life of the formulations and/or requiting stringent control of storage conditions. The aminosteroids also are known to be highly insoluble in water, even in salt form; such insolubility can seriously hamper efforts to utilize the compounds to their full potential. There is thus a serious need for improved pharmaceutical compositions comprising the aminosteriods and for methods for the stabilization of such pharmaceutical compositions.

Sustained release ophthalmic formulations of an ophthalmic drug and a high molecular weight polymer to form a highly viscous gel have been described in Schoenwald et al U.S. Pat. No. 4,271,143, issued Jun. 2, 1981 and Schoenwald et al U.S. Pat. No. 4,407,792, issued Oct. 4, 1983.

U.K. Patent Application GB 2007091 A, published May 16, 1979, describes an ophthalmic composition in the form of a gel comprising an aqueous solution of a carboxyvinyl polymer, a water-soluble basic substance and an ophthalmic drug, the gel having a pH of 5 to 8 and a viscosity of 1,000 centipoises to 100,000 centipoises at 20° C.

U.K. Patent Application GB 2013084 A, published Aug. 8, 1979, describes an aqueous gel for application to the conjunctival sac of the eye comprising an ophthalmic drug and a polymer having carboxylic or anhydride functional groups and a molecular weight in excess of 1,000,000, such as carboxypolymethylene, carboxyvinyl and ethylene maleic anhydride polymers.

Robinson U.S. Pat. No. 4,615,697, issued Oct. 7, 1986, discloses a controlled release composition and method of use based on a bioadhesive and a treating agent, such as an anti-inflammatory agent. The bioadhesive is a water-swellable, but water-insoluble, fibrous, cross-linked carboxy-functional polymer having a plurality of repeating units of which about 80 percent contain at least one carboxyl functionality and a cross-linking agent which is substantially free from polyalkenyl polyethers.

Davis et al copending application Ser. No. 07/544,518, filed Jun. 27, 1990, now U.S. Pat. No. 5,192,535 and assigned to the assignee hereof, describes formulation of lightly cross-linked polymers, preferably ones prepared by suspension or emulsion polymerizing at least about 90% by weight of a carboxyl-containing monoethylenically unsaturated monomer such as acrylic acid with from about 0.1% to about 5% by weight of a polyfunctional, and preferably difunctional, cross-linking agent such as divinyl glycol (3,4-dihydroxy-1,5-hexadiene), having a particle size of not more than 50 μm in equivalent spherical diameter, with an ophthalmic medicament, e.g., the steroid fluorometholone, into suspensions in aqueous medium in which the amount of polymer ranges from about 0.1% to about 6.5% by weight, based on the total weight of the aqueous suspension, the pH is from about 3.0 to about 6.5, and the osmotic pressure (osmolality or tonicity) is from about 10 mOsM to about 400 mOsM. These new topical ophthalmic medicament delivery systems have suitably low viscosities which permit them to be easily administered to the eye in drop form, and hence to be comfortably administered in consistent, accurate dosages. These suspensions will rapidly gel in the eye after coming into contact with the eye's tear fluid to a substantially greater viscosity than that of the originally-introduced suspension and thus remain in place for prolonged periods of time to provide sustained release of the ophthalmic medicament. See International Publication Number WO 92/00044 published Jan. 9, 1992, which claims priority from U.S. Ser. No. 07/544,518, U.S. Pat. No. 5,192,535 and see also International Publication No. WO 89/06964, published Aug. 10, 1989, which claims the priority of the parent and grandparent applications upon which Ser. No. 07/544,518 U.S. Pat. No. 5,192,535 is based.

It has not been heretofore suggested, however, that lightly cross-linked carboxy-containing polymers could be used to stabilize aminosteroids in pharmaceutical formulations. It was also not known that aminosteroids disclosed in International Publication No. WO 87/01706 and great grandparent U.S. Ser. No. 07/537,062 (now U.S. Pat. No. 5,124,154) would be compatible or stable with lightly cross-linked carboxy-containing polymers.

SUMMARY AND OBJECTS OF THE INVENTION

One object of the present invention is to provide a method for stabilizing amino-substituted steroid therapeutic agents in topical ophthalmic and other pharmaceutical formulations.

Still another object of the present invention is to provide topical ophthalmic and other pharmaceutical formulations of amino-substituted steroid therapeutic agents which have enhanced stability.

Another object of the present invention is to provide pharmaceutical formulations of amino-substituted steroid therapeutic agents suitable for administration by the various routes and for the various therapeutic purposes by and for which the steroid itself has been previously described.

In accord with the foregoing, the present invention provides a method for stabilizing an amino-substituted steroid therapeutic agent in a pharmaceutical formulation, said method comprising combining an amino-substituted steroid therapeutic agent selected from the group consisting of the $C_{20}$ through $C_{26}$ aminosteroids of the formula XI hereinbelow, and the pharmaceutically acceptable salts, hydrates and solvates thereof, with an effective stabilizing amount of lightly cross-linked carboxy-containing polymer in an aqueous medium.

In another aspect, the present invention provides a pharmaceutical composition comprising an amino-substituted steroid therapeutic agent selected from the group consisting of the $C_{20}$ through $C_{26}$ aminosteroids of the formula XI hereinbelow, and the pharmaceutically acceptable salts, hydrates and solvates thereof, and an effective stabilizing amount of lightly cross-linked carboxy-containing polymer, in an aqueous medium.

DETAILED DESCRIPTION OF THE INVENTION AND THE PREFERRED EMBODIMENTS

In all aspects of the present invention, the amino-substituted steroid therapeutic agents employed herein are the $C_{20}$ through $C_{26}$ aminosteroids of formula XI (especially those which exhibit antioxidant functions), as set forth in International Publication No. WO 87/01706 and in applicants' parent Ser. No. 07/933,574 and grandparent Ser. No. 07/838,875 and great grandparent Ser. No. 07/537,062 (now U.S. Pat. No. 5,124,154), all of which are incorporated by reference herein in their entireties and relied upon. The intended aminosteroids have the formula

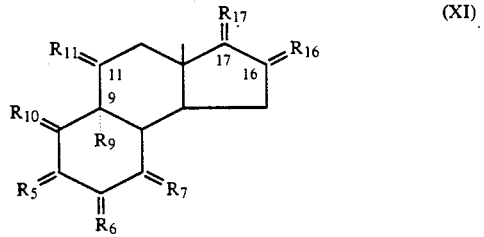

where:

(A-I) $R_6$ is $\alpha$-$R_{61}$:$\beta$-$R_{62}$, $R_{10}$ is $\alpha$-$R_{101}$:$\beta$-$R_{102}$ and $R_7$ is $\alpha$-H: $\beta$-H, where one of $R_{61}$ and $R_{62}$ is —H, and the other is —H, —F, or $C_1$-$C_3$ alkyl, $R_{102}$ is —$CH_3$, $R_{101}$ and $R_5$ taken together are —$(CH_2)_2$—C(—$R_{33}$)—CH= or —CH—CH—CO—CH=, where $R_{33}$ is =O or $\alpha$-H: $\beta$-$OR_{34}$ or $\alpha$-$OR_{34}$: $\beta$-H, where $R_{34}$ is —H, —P(=O)-$(OH)_2$, —CO—$CH_3$, —CO—$C_2H_5$, —CO—$C_6H_5$, —CO—O—$CH_3$ or —CO—O—$C_2H_5$;

(A-II) $R_5$ is $\alpha$-$R_{53}$:$\beta$-$R_{54}$, $R_6$ is $\alpha$-$R_{63}$:$\beta$-$R_{64}$, $R_{10}$ is $\alpha$-$R_{103}$:$\beta$-$R_{104}$ and $R_7$ is $\alpha$-H: $\beta$-H, where one of $R_{63}$ and $R_{64}$ is —H, and the other taken together with one of $R_{53}$ and $R_{54}$ forms a second bond between $C_5$ and $C_6$, $R_{104}$ is —$CH_3$, $R_{103}$ and the other of $R_{53}$ and $R_{54}$ taken together are —$(CH_2)_2$—C(H)(OH)—$CH_2$—or —$(CH_2)_2$—C[HI][OP(=O)—$(OH)_2$]—$CH_2$—;

(A-III) $R_{10}$ and $R_5$ taken together are =CH—CH= C($OR_3$)—CH= where $R_3$ is —H, —P(=O)$(OH)_2$, $C_1$-$C_3$ alkyl, —CO—H, $C_2$-$C_4$ alkanoyl or benzyl, $R_6$ is $\alpha$-$R_{65}$:$\beta$-$R_{66}$ where one of $R_{65}$ and $R_{66}$ is —H, and the other is —H, —F, or $C_1$-$C_3$ alkyl and $R_7$ is $\alpha$-H: $\beta$-H;

(A-IV) $R_5$ is $\alpha$-$R_{57}$:$\beta$-$R_{58}$, $R_6$ is $\alpha$-$R_{67}$:$\beta$-$R_{68}$, $R_7$ is $\alpha$-H: $\beta$-H and $R_{10}$ is $\alpha$-$R_{107}$:$\beta$-$R_{108}$, where one of $R_{57}$ and $R_{58}$ is —H, $R_{107}$ and the other of $R_{57}$ and $R_{58}$ taken together are —$(CH_2)_2$—C(=$R_{33}$)—$CH_2$, where $R_{33}$ is as defined above, $R_{108}$ is —$CH_3$, where one of $R_{67}$ and $R_{68}$ is —H and the other is —H, —F, or $C_1$-$C_3$ alkyl;

(A-V) $R_6$ is $R_{69}$:$R_{610}$, $R_7$ is $R_{79}$:$R_{710}$, $R_{10}$ is $\alpha$-$R_{109}$:$R_{1010}$, where one of $R_{69}$ and $R_{610}$ is —H and the other taken together with one of $R_{79}$ and $R_{710}$ forms a second bond between $C_6$ and $C_7$, and the other of $R_{79}$ and $R_{710}$ is —H, $R_{1010}$ is —$CH_3$, $R_{109}$ and $R_5$ taken together are —$(CH_2)_2$—C(=$R_{33}$)—CH= or —CH= CH—CO—CH=, where $R_{33}$ is as defined above; where:

(C-I) $R_{11}$ is $\alpha$-$R_{111}$:$\beta$-$R_{112}$, where one of $R_{111}$ and $R_{112}$ is taken together with $R_9$ to form a second bond between $C_9$ and $C_{11}$ and the other of $R_{111}$ and $R_{112}$ is —H;

(C-II) $R_9$ is —Cl and $R_{11}$ is =O or $\alpha$-H:$\beta$-$R_{114}$ where $R_{114}$ is —Cl or —OH;

(C-III) $R_9$ is —H or —F and $R_{11}$ is =O or $\alpha$-$R_{115}$:$\beta$-$R_{116}$, where one of $R_{115}$ and $R_{116}$ is —H, and the other of $R_{115}$ and $R_{116}$ is —H, —OH or $C_1$-$C_{12}$ alkoxy;

(C-IV) $R_9$ is —H or —F and $R_{11}$ is $\alpha$-O—CO—$R_{117}$: $\beta$-H, where $R_{117}$ is (A) $C_1$-$C_3$ alkyl,
(B) $C_1$-$C_{12}$ alkoxy,
(C) furanyl,
(D) —$NR_{122}R_{123}$, where one of $R_{122}$ and $R_{123}$ is —H, methyl or ethyl and the other is —H, $C_1$-$C_4$ alkyl or phenyl,
(E) —$X_3$—$X_1$, where $X_3$ is —O—or a valence bond, where $X_1$ is phenyl optionally substituted with 1 through 2 —Cl, —Br, $C_1$-$C_3$ alkoxy, —COOH, —$NH_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino and —NH— CHO or with 1 —F or —$CF_3$;

where:

(D-I) $R_{16}$ is $R_{161}$:$R_{162}$ and $R_{17}$ is $R_{171}$:$R_{172}$, where one of $R_{161}$ and $R_{162}$ is —H or —$CH_3$ and the other taken together with one of $R_{171}$ and $R_{172}$ forms a second bond between $C_{16}$ and $C_{17}$, and the other of $R_{171}$ and $R_{172}$ is —C(=Z)—$(CH_2)_n$—$NR_{21}R_{210}$, where Z is =O, =$CH_2$ or $R_{179}$:—H where $R_{179}$ is —H or —$CH_3$, where n is 0 through 6, where (A) $R_{21}$ is (1) —$(CH_2)_m$—$NR_{211}$—$X_2$, where m is 2, 3 or 4, where $R_{211}$ is —H or $C_1$-$C_3$ alkyl, where $X_2$ is: [A]
(a) pyridin-2-, 3- or 4-yl or the N-oxide thereof optionally substituted by 1 or 2 $R_{212}$, being the same or different, where $R_{212}$ is
  (i) —F,
  (ii) —Cl,
  (iii) —Br,
  (iv) $C_1$-$C_5$ alkyl,
  (v) —CH—CH=$CH_2$,
  (vi) —X, where $X_1$ is as defined above,
  (vii) —$NR_{213}R_{213}$ where the $R_{213}$'s are the same or different and are —H, $C_1$-$C_3$ alkyl or —$CH_2$—CH=$CH_2$,
  (viiα) *$CH_2$—$(CH_2)_q$—$CH_2$—N*—where the atoms marked with an asterisk (*) are bonded to each other resulting in the formation of a ring, where q is 1 through 5,
  (viiβ) *$CH_2$—$CH_2$—$(CH_2)_c$—G—$(CH_2)_d$—$CH_2$—$CH_2$—N*— where the atoms marked with an asterisk (*) are bonded to each other resulting in the formation of a ring, where G is —O—, —S—, —SO—, —$SO_2$— or —$NHR_{214}$, where $R_{214}$ is —H, $C_1$-$C_3$ alkyl, or $X_1$ as defined above, where c and d are the same or different and are 0 through 2 with the proviso that the total number of ring carbon atoms is 4, 5 or 6, [a]

(ix) 3-pyrrolin-1-yl, [b]
(x) pyrrol-1-yl optionally substituted with $C_1$-$C_3$ alkyl, [c]
(xi) piperidin-1-yl optionally substituted with 1 or 2 $C_1$-$C_3$ alkyl, [d]
(xii) 1,2,3,6-tetrahydropyridin-1-yl, [e]
(xiii) 1-hexamethyleneimino containing a 3- or 4-double bond or 3- and 5-double bonds, [f]
(xiv) 1,4-dihydro-1-pyridinyl substituted in the 4 position by two $C_1$-$C_3$ alkyl being the same or different, [g]
(xv) —OH,
(xvi) $C_1$-$C_3$ alkoxy,
(xvii) —$NR_{217}$—$(CH_2)_e$—Q where Q is 2-pyridinyl where $R_{217}$ is —H or $C_1$-$C_3$ alkyl and e is 0 through 3 (1)
(xviii) pyridin-2-, 3- or 4-yl, (b) 1,3,5-triazin-4-yl or the N-oxide thereof optionally substituted at the 2- and/or 6-position with $R_{212}$ as is defined above, (4)
(c) pyrimidin-4-yl or the N-oxide thereof optionally substituted at the 2- and/or 6-position with $R_{212}$ as is defined above, (5)
(d) pyrimidin-2-yl optionally substituted at the 4- and/or 6-position with 1 or 2 $R_{212}$ as is defined above, (6)
(e) pyrazin-2-yl optionally substituted with 1 or 2 $R_{212}$ as is defined above, (7)
(f) imidazol-2-yl optionally substituted in the 1 position with $C_1$-$C_3$ alkyl or —$X_1$, where $X_1$ is as defined above, and further optionally substituted with 1 or 2 $R_{212}$ as defined above, (8)
(g) 1,3,4-triazol-2-yl optionally substituted in the 1 position with $C_1$-$C_3$ alkyl or —$X_1$, where $X_1$ is as defined above, and further optionally substituted with $R_{212}$ as defined above, (9)
(h) imidazol-4- or 5-yl optionally substituted in the 1 position with $C_1$-$C_3$ alkyl or —$X_1$, where $X_1$ is as defined above, and further optionally substituted with 1 or 2 $R_{212}$ as defined above, (10)
(i) benzo[b]thien-2-yl, (12a)
(j) indol-2-yl, (12b)
(k) benzo[b]thiazol-2-yl, (12c)
(l) benzimidazol-2-yl, (12d)
(m) 4-[2-[4-[2,6-bis(1-pyrrolidinyl)-4-pyrimidinyl]-1-piperazinyl]ethyl]piperazinyl, (13)
(n) 1,2,4-triazin-3-yl optionally substituted at the 5- and/or 6-position with $R_{212}$ as is defined above, (14)

(2) (1-piperazinyl)-($C_2$-$C_4$)alkyl optionally substituted in the 4-position with —$X_1$ or —$X_2$ as defined above, [B]
(3) —$X_2$, as defined above, [O]
(4) —$(CH_2)_m$—$X_4$ where m is as defined above and where $X_4$ is
  (a) —O—$CH_2CH_2$—Y, where Y is $C_1$-$C_3$ alkylamino, di($C_1$-$C_3$)alkylamino where the alkyl groups are the same or different, $C_3$-$C_6$ alkyleneimino, optionally substituted with 1 or 2 $C_1$-$C_3$ alkyl,
  (b) —$NR_{220}CH_2CH_2$—Y, where $R_{220}$ is —H or $C_1$-$C_3$ alkyl and Y is as defined above,
  (c) —$(CH_2)_g$—$N(R_{220})$—$X_2$, where g is 2, 3 or 4, and where $R_{220}$ and $X_2$ are as defined above, [H]

(5) —$(CH_2)_m$—$NR_{222}R_{223}$, where $R_{222}$ is —H or $C_1$-$C_3$ alkyl and $R_{223}$ is —$X_1$ or —$X_2$ as defined above, or $R_{222}$ and $R_{223}$ are taken together with the attached nitrogen atom to form a saturated mononitrogen $C_3$-$C_6$ heterocyclic ring and where m is as defined above, [I]
(6) —$(CHCH_3)_b$—$(CH_2)_f$—$R_{224}$, where b is 0 and f is 1 through 3 or b is one and f is 0 through 3, where $R_{224}$ is phenyl substituted with 1 through 3 —OH, $C_1$-$C_3$ alkoxy, —$NR_{225}R_{226}$ where $R_{225}$ and $R_{226}$ are the same or different and are —H, $C_1$-$C_3$ alkyl or are taken together with the attached nitrogen atom to form a $C_4$-$C_7$ cyclic amino ring, [J]
(7) —$(CH_2)_i$—$X_2$, where i is 1 through 4 and $X_2$ is as defined above, [K]
(8) (1-piperazinyl)acetyl substituted in the 4-position by $X_2$ where $X_2$ is as defined above, [L]
(9) (1-piperazinyl)carbonylmethyl substituted in the 4-position by —$X_2$ where $X_2$ is as defined above, and [M]

(B) $R_{210}$ is
(1) —H,
(2) $C_1$-$C_3$ alkyl,
(3) $C_5$-$C_7$ cycloalkyl,
(4) —$(CH_2)_m$—$NR_{211}$—$X_2$, where m, $R_{211}$ and $X_2$ are as defined above, [A]
(5) (1-piperazinyl)—($C_2$-$C_4$)alkyl optionally substituted in the 4-position with —$X_1$ or —$X_2$ as defined above, [B]
(6) —$(CH_2)_m$—$X_4$, where m and $X_4$ are as defined above, [H]
(7) —$(CH_2)_m$—$NR_{222}R_{223}$, where m, $R_{222}$ and $R_{223}$ are as defined above, [I]
(8) —$(CHCH_3)_b$—$(CH_2)_f$—$R_{224}$, where b, f and $R_{224}$ are as defined above, [J]

(C) $R_{21}$ and $R_{210}$ are taken together with the attached nitrogen atom to form a heterocyclic ring selected from the group consisting of
(1) 2-(carboxy)-1-pyrrolidinyl optionally as the $C_1$-$C_3$ alkyl ester or as a pharmaceutically acceptable salt, [C-1]
(2) 2-(carboxy)-1-piperidinyl optionally as the $C_1$-$C_3$ alkyl ester or as a pharmaceutically acceptable salt [C-2]
(3) 2-(carboxy)-1-hexamethyleneimino optionally as the $C_1$-$C_3$ alkyl ester or as a pharmaceutically acceptable salt, [C-3]
(4) 2-(carboxy)-1-heptamethylene-imino optionally as the $C_1$-$C_3$ alkyl ester or as a pharmaceutically acceptable salt, [C-4]
(5) 1-piperazinyl substituted in the 4-position with $R_{228}$—CO—$(CH_2)_j$— where $R_{228}$ is —$X_1$, —$NR_{229}X_1$, or 2-furanyl, where $R_{229}$ is —H or $C_1$-$C_3$ alkyl, where j is 0 through 3 and $X_1$ is as defined above, [D]
(6) 1-piperazinyl substituted in the 4-position with $X_2$—$(CH_2)_j$—, where $X_2$ and j are as defined above, [E]
(7) 1-piperazinyl substituted in the 4-position with $X_1$—$(CH_2)_j$—, where $X_1$ and j are as defined above, [F]
(8) 4-hydroxy-1-piperidinyl substituted in the 4-position with $X_1$ as defined above, [G]
(9) 1-piperazinyl substituted in the 4-position with $X_2$—$NR_{229}$—CO—$(CH_2)_i$—, where $X_2$, $R_{229}$ and i are as defined above; [N]

(D-II) $R_{16}$ is $\alpha$-$R_{163}$:$\beta$-$R_{164}$ where one of $R_{163}$ and $R_{164}$ is —H and the other is —H, —F, —$CH_3$ or —OH, and $R_{17}$ is —CH—$(CH_2)_p$—$NR_{21}R_{210}$, where p is 1 or 2, where $R_{21}$ and $R_{210}$ are as defined above;

(D-III) $R_{16}$ is $\alpha$-$R_{165}$:$\beta$-$R_{166}$ and $R_{17}$ is $\alpha$-$R_{175}$:$\beta$-$R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2$-$C_7$ alkanoyloxy or —O—CO—$X_1$, where $X_1$ is as defined above, and where $R_{176}$ is —C(=Z)—$(CH_2)_n$—$NR_{21}R_{210}$, where Z, n, $R_{21}$ and $R_{210}$ are as defined above;

(D-IV) the 16, 17-acetonide of a compound where $R_{165}$ is —OH, $R_{166}$ is —H, $R_{175}$ is —OH and $R_{176}$ is —C(=Z)—$(CH_2)_n$—$NR_{21}R_{210}$, where Z, n, —$R_{21}$ and $R_{210}$ are as defined above;

and pharmaceutically acceptable salts thereof, and hydrates and solvates thereof;
with the following overall provisos that:

(I) one of $R_{161}$ or $R_{162}$ is taken together with one of $R_{171}$ or $R_{172}$ to form a second bond between $C_{16}$ and $C_{17}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$: $\beta$-$R_{1010}$, (II) $R_{17}$ is —CH—$(CH_2)_p$—$NR_{21}R_{210}$, only when $R_{10}$ is $\alpha$-$R_{101}$:$\beta$-$R_{102}$, a-$R_{103}$:$\beta$-$R_{104}$, $\alpha$-$R_{107}$:$\beta$-$R_{108}$ or $\alpha$-$R_{109}$:$\beta$-$R_{1010}$, (III) $R_5$ and $R_{10}$ taken together are =CH—CH=C($OR_3$)—CH=, only when $R_{17}$ is $\alpha$-$R_{175}$:$\beta$-$R_{176}$ or the 16, 17-acetonide of a compound where $R_{16}$ is $\alpha$-OH: $\beta$-H and $R_{17}$ is $\alpha$-OH: $\beta$-C(=Z)—$(CH_2)_n$—$NR_{21}R_{210}$, and (IV) $R_5$ is $\alpha$-$R_{57}$:$\beta$-$R_{58}$, only when $R_{17}$ is $\alpha$-$R_{175}$:$\beta$-$R_{176}$ or $\alpha$-OH: $\beta$-C—(=Z)—$(CH_2)_n$—$NR_{21}R_{210}$, or the 16, 17-acetonide thereof.

More preferred are the $C_{21}$ aminosteroids of formula XI, especially those which inhibit lipid peroxidation. Most preferred are the 21-[4-(substituted-4-pyrimidinyl)-1-piperazinyl]-steroids, such as U-74006 (21-[4-(2,6-dipyrrolidinyl-4-pyrimidinyl)-16α-piperazinyl]- 16α-methylpregna-1,4,9(11)-triene-3,20-dione), and the 21-[4-(substituted-2-pyridinyl)-1-piperazinyl]-steroids, such as U-74500 (21-[4-[5,6-bis(-diethylamino)-2-pyridinyl]-1-piperazinyl]-16α-methylpregna-1,4,9(11)-triene-3,20-dione) and U-75412 (21-[4(3-ethylamino-2-pyridinyl)-1-piperazinyl]-16α-methylpregna-1,4,9(11)-triene-3,20-dione), all, when in the unformulated state, preferably as a solid, preferably crystalline, preferably relatively non-hygroscopic and pharmaceutically acceptable salts, such as the methanesulfonate salt of U74006 (U-74006F), the hydrochloride of U-74500 (U-74500A), and the hydrochloride or maleic acid salt of U-75412 (U-75412A and U-75412E, respectively); See Braughler et al, *Biochemical Pharmacology* 37:3853-3860 (1988). The following are illustrative structures.

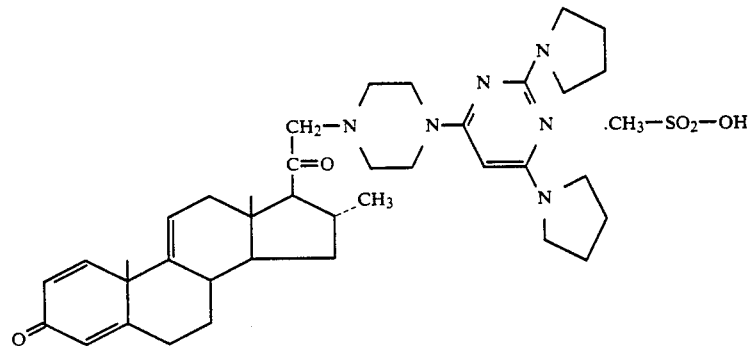

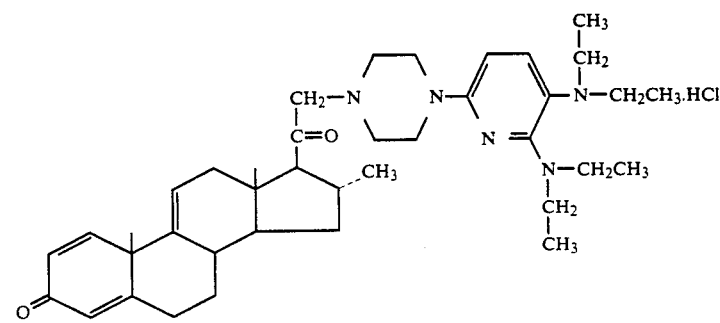

-continued

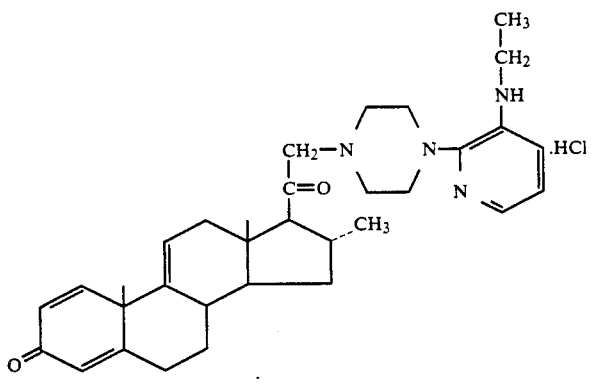

The above-preferred amino steroids are all exemplified as 21-substituted-16α-methylpregna-1,4,9(11)-triene-3,20-diones. However, the steroidal portion of these may be modified without substantially altering their preferred nature. Thus, a class of preferred $C_{21}$ amino-substituted steroids may be represented by the formula I, below

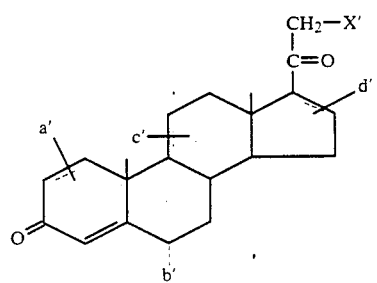

where:

a' is selected from the group 1,2-dihydro (saturated) and 1,2-dehydro (1,2-double bond);

b' is selected from the group 6α-H, 6α-methyl and 6α-fluoro;

c' is selected from the group 9, 11-dihydro (saturated), 9(11)-dehydro (double bond), 9α-H-11α-OH-11β-H, 9α-H-11β-OH-11α-H, 9α-H-11-keto, 9α-F-11β-OH-11α-H and 9α-F-11-keto;

d' is selected from the group 16α-methyl-16β-H-17α-H, 16β-methyl-16β-H-17α-H, 16-H₂-17α-H, 16-H-16,17-dehydro (double bond), and 16-methyl-16,17-dehydro. Less preferably, a 17α-OH group can be present instead of 17α-H when d' is not 16-H-16,17-dehydro or 16-methyl-16,17-dehydro;

and where:

X' is selected from the complex 21-amino substituents X1' and X2'
where

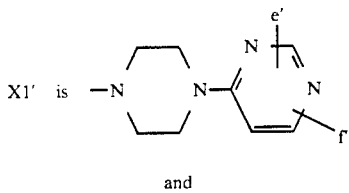

and

X2' is where e' and f' may be the same or different and are selected from the group: H, NHR1' and NR1'R2', where R1' and R2' are C1 to C3 lower alkyl or R1' and R2', taken together with N, constitute a heterocyclic ring; preferably 1-ethyleneimino, 1-trimethyleneimino, 1-pyrrolidinyl, 1-piperidinyl, 1-morpholinyl and 1-(4-methyl)piperazinyl.

It is within the ability of those skilled in the art to determine without undue experimentation which of the foregoing aminosteroids will function as antioxidant agents. International Publication No. WO 87/01706 indicates that the arachidonic acid $LD_{50}$ test of Kohler, *Thrombosis Res.*, 9, 67 (1976) identifies compounds which are antioxidants, and the publication also references Pryor in *Methods of Enzymology*, 105, 293 (1984) for another method useful for determining which particular compounds inhibit lipid peroxidation.

Pharmaceutically acceptable salts of the aminosteroids of formula (XI) are frequently preferred over the free base form because the salts are more soluble in water and form crystals which are better suited to pharmaceutical use. Preferred salts are those prepared by reacting the free base of the aminosteroid of formula (XI) with an approximately stoichiometrical amount of a pharmaceutically acceptable acid such as hydrochloric, hydroiodiic, hydrobromic, phosphoric, sulfuric, acetic, citric, lactic, succinic, benzoic, pamoic, salicylic, cyclohexanesulfamic, methanesulfonic, p-toluenesulfonic, naphthalenesulfonic, maleic, oxalic, fumaric or the like. Preferred salts are those of hydrochloric, methanesulfonic, maleic and fumaric acids.

Equivalent to the steroids of formula (XI) and their pharmaceutically acceptable acid addition salts for the purposes of this invention are the pharmaceutically acceptable hydrates or solyates thereof, in which form they can be isolated.

The lightly cross-linked carboxy-containing polymers for use in the present invention are lightly cross-linked polymers of acrylic acid or the like and are, in general, well-known in the art. See, for example, Robinson U.S. Pat. No. 4,615,697, and International Publication No. WO 89/06964, referred to hereinabove. These polymers are also described in Davis et al copending application Ser. No. 07/544,518, likewise referred to hereinabove.

In a preferred embodiment, suitable polymers are ones prepared from at least about 90% and preferably from about 95% to about 99.9% by weight, based on the total weight of monomers present, of one or more carboxyl-containing monoethylenically unsaturated monomers. Acrylic acid is the preferred carboxyl-containing monoethylenically unsaturated monomer, but other unsaturated, polymerizable carboxyl-containing monomers, such as methacrylic acid, ethacrylic acid, $\beta$-methylacrylic acid (crotonic acid), cis-$\alpha$-methylcrotonic acid (angelic acid), trans-$\alpha$-methylcrotonic acid (tiglic acid), $\alpha$-butylcrotonic acid, $\alpha$-phenylacrylic acid, $\alpha$-benzylacrylic acid, $\alpha$-cyclohexylacrylic acid, $\beta$-phenylacrylic acid (cinnamic acid), coumaric acid (o-hydroxycinnamic acid), umbellic acid (p-hydroxycoumaric acid), and the like can be used in addition to or instead of acrylic acid.

Such polymers are cross-linked by using a small percentage, i.e., less than about 5%, such as from about 0.01% or from about 0.5% to about 5%, and preferably from about 0.2% to about 3%, based on the total weight of monomers present, of a polyfunctional cross-linking agent. Included among such cross-linking agents are non-polyalkenyl polyether difunctional cross-linking monomers such as divinyl glycol; 3,4-dihydroxy-hexa-1,5-diene; 2,5-dimethyl-1,5-hexadiene; divinylbenzene; N,N-diallylacrylamide; N,N-diallylmethacrylamide and the like. Also included are polyalkenyl polyether cross-linking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053. Diolefinic non-hydrophilic macromeric cross-linking agents having molecular weights of from about 400 to about 8,000, such as insoluble di- and polyacrylates and methacrylates of diols and polyols, diisocyanate-hydroxyalkyl acrylate or methacrylate reaction products, and reaction products of isocyanate terminated prepolymers derived from polyester diols, polyether diols or polysiloxane diols with hydroxyalkylmethacrylates, and the like, can also be used as the crosslinking agents; see, e.g., Mueller et al U.S. Pat. Nos. 4,192,827 and 4,136,250.

The lightly cross-linked polymers can of course be made from a carboxyl-containing monomer or monomers as the sole monoethylenically unsaturated monomer present, together with a cross-linking agent or agents. They can also be polymers in which up to about 40%, and preferably from about 0% to about 20% by weight, of the carboxyl-containing monoethylenically unsaturated monomer or monomers has been replaced by one or more non-carboxyl-containing monoethylenically unsaturated monomers containing only physiologically (and, where appropriate, ophthalmologically) innocuous substituents, including acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like, vinyl acetate, N-vinylpyrolidone, and the like; see Mueller et al U.S. Pat. No. 4,548,990 for a more extensive listing of such additional monoethylenically unsaturated monomers. Particularly preferred polymers are lightly cross-linked acrylic acid polymers wherein the cross-linking monomer is 3,4-dihydroxyhexa-1,5-diene or 2,5-dimethylhexa-1,5-diene.

An especially preferred lightly cross-linked carboxy-containing polymer for use herein is polycarbophil, particularly NOVEON AA1, a carboxyl-containing polymer prepared by suspension polymerizing acrylic acid and divinyl glycol. NOVEON AA1 (also called Carbopol 976) is commercially available from The B.F. Goodrich Company. A different preferred lightly cross-linked carboxy-containing polymer for use herein is Carbopol 974P which is prepared using a different polyfunctional cross-linking agent of the polyalkenyl polyether type.

The lightly cross-linked polymers used in practicing this invention are preferably prepared by suspension or emulsion polymerizing the monomers, using conventional free radical polymerization catalysts, to a dry particle size of not more than about 50 $\mu$m in equivalent spherical diameter; e.g., to provide dry polymer particles ranging in size from about 1 to about 30 $\mu$m, and preferably from about 3 to about 20 $\mu$m, in equivalent spherical diameter. In general, such polymers will range in molecular weight estimated to be from about 250,000 to about 4,000,000, and preferably from about 500,000 to about 2,000,000.

The aminosteroids can be administered by a variety of routes for the treatment or prevention of a variety of conditions, as noted in International Publication No. WO 87/01706 and in applicants' parent Ser. No. 07/933,574, U.S. Pat. No. 5.209,906 grandparent Ser. No. 07/838,875 abandoned and great grandparent Ser. No. 07/537,062, U.S. Pat. No. 5.124.154 and as discussed in more detail below. For particular routes of administration, certain characteristics of the lightly cross-linked polymers need to be carefully controlled. Thus, for example, aqueous suspensions containing polymer particles prepared by suspension or emulsion polymerization whose average dry particle size is appreciably larger than about 50 $\mu$m in equivalent spherical diameter are less comfortable when administered to the eye than suspensions otherwise identical in composition containing polymer particles whose equivalent spherical diameters are, on the average, below about 50 $\mu$m. Moreover, above the average 50 $\mu$m size, the advantage of substantially increased viscosity after administration to the eye which is disclosed in applicants' parent and grandparent applications is not realized. It has also been discovered that lightly cross-linked polymers of acrylic acid or the like prepared to a dry particle size appreciably larger than about 50 $\mu$m in equivalent spherical diameter and then reduced in size, e.g., by mechanically milling or grinding, to a dry particle size of not more than about 50 $\mu$m in equivalent spherical diameter do not work as well as polymers made by suspension or emulsion polymerization. While we do not wish to be bound by any theory or mechanism advanced to explain the functioning of this aspect of invention, one possible explanation for the difference of such mechanically milled or ground polymer particles as the sole particulate polymer present is that grinding disrupts the spatial geometry or configuration of the larger than 50 $\mu$m lightly cross-linked polymer particles, perhaps by removing uncross-linked branches from polymer chains, by producing particles having sharp edges or protrusions, or by producing ordinarily too broad a range of particle sizes to afford satisfactory delivery system performance. A broad distribution of particle sizes will impair the viscosity-gelation relationship, which, as noted in applicants's parent and grandparent applications, is important in the case of eye administration. In any event, such mechanically reduced particles are less easily hydratable in aqueous suspension than particles prepared to the appropriate size by suspension or emulsion polymerization, and also are less able to gel in the eye under the influence of tear fluid to a sufficient extent and are less comfortable once gelled than gels produced in the eye using the polymers made by suspension or emulsion polymerization. However, up to about 40% by weight, e.g., from about 0% to over 20% by weight, based on the total weight of lightly cross-linked particles present, of such milled or ground polymer particles can be admixed with solution or emulsion polymerized polymer particles having dry particle diameters of not more than about 50 μm when practicing this invention. Such mixtures will also provide satisfactory viscosity levels in the ophthalmic medicament delivery systems and in the in situ gels formed in the eye coupled with ease and comfort of administration and satisfactory sustained release of the aminosteroid to the eye, particularly when such milled or ground polymer particles, in dry form, average from about 0.01 to about 30 μm, and preferably from about 1 to about 5 μm, in equivalent spherical diameter.

In the most preferred embodiment of the invention, the particles have a narrow particle size distribution within a 10 μm band of major particle size distribution which contains at least 80%, more preferably at least 90%, most preferably at least 95% of the particles. Also, there is no more than 20%, preferably no more than 10%, and most preferably no more than 5% particles of a size below 1 μm. The presence of large amounts of such fines has been found to inhibit the desired gelation upon eye contact. Apart from that, the use of a monodispersion of particles will give maximum viscosity and an increased eye residence time of the ophthalmic medicament delivery systems for a given particle size. Monodisperse particles having a particle size of 30 μm and below are most preferred. Good particle packing is aided by a narrow particle size distribution.

Applicants' parent Ser. No. 07/933,574, U.S. Pat. No. 5,209,926, grandparent Ser. No. 07/838,875 and great grandparent Ser. No. 07/537,062 U.S. Pat. No. 5,124,154 disclose formulation of the hereinabove-described aminosteroids with an appropriate inert vehicle or carrier for prevention or treatment of ophthalmic diseases or disorders (discussed in more detail below). Topical, intraocular and systemic routes of administration are described. The term "inert vehicle" is broadly used in those earlier applications to optionally include adjuvants, preservatives, buffers, demulcents and anything else that is essentially inert relative to the therapeutic function (particularly the antioxidant function) of the aminosteroids as that function relates to eye tissue. The earlier applications teach that topical formulations should generally include between 0.01 and 10% by weight, preferably between 0.1 and 5% by weight, of the amino-substituted steroid therapeutic agent in a suitable polymeric carder. Suitable polymeric carriers are taught to include lightly cross-linked carboxy-containing polymers (such as polycarbophil), dextran, cellulose derivatives, polyethyleneglycol 400 and other polymeric demulcents. Other additions taught as desirably included in the topical formulations include sodium chloride, EDTA (disodium edetate), surfactants, and preservatives such as BAK (benzalkonium chloride). The earlier applications further teach that aqueous solutions and suspensions for liquid oral administration will typically contain between about 0.05 and 5.0% by weight, preferably between 0.1 and 2.0% by weight of the amino-substituted steroid therapeutic agent; that suitable adjuvants which may be used as carriers to provide wetability and stability include propylene glycol, lightly cross-linked carboxy-containing polymers such as polycarbophil, ethyl cellulose, hydroxypropyl cellulose and methyl cellulose; and that other additives, including sodium edetate, methyl and propyl parabens, flavoring agents and colorants may also be employed, if desired. Examples 7 and 8 in the parent and grandparent applications detail the preparation of topical compositions containing the aminosteroid U-74006F, U-74500A or U-75412A and a polycarbophil (Carbopol 976). A viscosity of 5,000 cps or greater is noted in Example 7. Sodium chloride, EDTA, sodium hydroxide and, optionally, the preservative benzalkonium chloride are also present in the compositions.

It has now been found that the aminosteroid therapeutic agents which are as defined herein as well as in the parent and grandparent and great grandparent applications can be remarkably stabilized by combining the steroid with an effective stabilizing amount of lightly cross-linked carboxy-containing polymer in an aqueous medium. Selected compositions disclosed in the parent and grandparent applications have thus been found to possess exceptional stability. This stability is believed to be achieved via an ionic interaction between the aminosteroid and the lightly cross-linked carboxy-containing polymer (e.g., polyacrylic hydrogel). As such, this exceptional stability characterizes pharmaceutical compositions comprising the aminosteroid and lightly cross-linked carboxy-containing polymer in aqueous medium, regardless of the intended route of administration or the purpose for which the composition is to be administered.

As noted in applicants' parent, grandparent and great grandparent applications, the aminosteroids are themselves capable of oxidative degradation and it is therefore desirable that the formulations including them avoid oxidation and excessive exposure to light. The parent and grandparent applications further teach that the formulations are preferably prepared in an anaerobic environment by making all formulations under an inert gas, and the finished formulations are preferably stored in opaque or brown containers to protect them from light exposure, and under an inert atmosphere. Such precautions are generally unnecessary for aminosteroid-containing pharmaceutical formulations which also contain an effective stabilizing amount of lightly cross-linked carboxy-containing polymers (such as polycarbophil), as provided by the present invention.

In a typical method for stabilizing aminosteroids in accord with the present invention, an effective stabilizing amount of the polymer is slowly dispersed in water and stirred, typically for a period of from about 15 minutes to 2 hours. This amount is generally from about 0.1% to about 2.0% by weight of the final composition, although greater amounts of the polymer, e.g. up to about 6.5% by weight of the total composition, can be present in the composition, particularly if a more viscous formulation is desired; this amount can also be expressed as a weight to weight ratio of polymer to aminosteroid of from about 1:10 to about 20:1. Sodium chloride (from about 0 to 0.9% by weight) is added to adjust osmolality and, optionally, EDTA may be added to complex metal ions. This mixture is generally heated (typically autoclaved) for a period of from about 30 to about 90 minutes, then cooled. It is preferred to adjust the pH of the mixture to be above about 6. This may be done by addition of a suitable base such as sodium hydroxide. At the same time, the aminosteroid component (from about 0.01 to about 10.0% by weight of the final composition) is dissolved in a strong acid solution (e.g. aqueous hydrochloric acid), using care not to lower the pH much below pH 2 so as not to hydrolyze the aminosteroid. The acidic aminosteroid solution is then added slowly to the polymer dispersion, the pH is adjusted to around pH 7 with sodium hydroxide and water is added as needed. Obtained in this manner, the formulation is viscous and the aminosteroid is suspended therein. Viscosity generally increases with increasing concentrations of polymer.

Stabilized pharmaceutical compositions prepared in accord with the present invention as described immediately above are thus obtained as viscous aqueous suspensions and are capable of sustained release of the aminosteroid therapeutic agent. Because of these characteristics, the compositions so obtained are of particular value as topical delivery systems, especially as ophthalmic and dermal aminosteroid delivery systems (although they can be administered by other routes as well).

In accordance with one preferred form of the invention, a stabilized sustained release aminosteroid delivery system comprises an aqueous suspension at a pH of from about 3 to about 9 (preferably 5 to 8) and an osmotic pressure of from about 10 to about 400 mOsM containing from about 0.1% to about 6.5% by weight, based on the total weight of the suspension, of a lightly cross-linked, carboxyl-containing polymer prepared by polymerizing one or more carboxyl-containing monoethylenically unsaturated monomers and less than about 5% by weight of a cross-linking agent, such weight percentages of monomers being based on the total weight of monomers polymerized. Typically, the suspension has an initial viscosity of from about 1,000 to about 30,000 centipoises and is administrable to the eye in drop form, or in the form of a ribbon at a viscosity of from about 30,000 to about 100,000 centipoises, but considerably higher viscosities are acceptable for topical routes of administration other than ophthalmic, e.g. dermal, and local routes such as nasal, buccal, rectal and vaginal. The polymer has an average particle size of not more than about 50 μm, preferably not more than about 30 μm, in equivalent spherical diameter. In the case of topical ophthalmic delivery systems, the pH of the suspension is from about 5 to about 9. The viscous gel can remain in the eye for a prolonged period of time so as to release the aminosteroid therapeutic agent contained therein in sustained fashion.

The polymer is preferably prepared from at least about 50% by weight, more preferably at least about 90% by weight, of one or more carboxyl-containing monoethylenically unsaturated monomers. Desirably, the polymer is prepared by suspension or emulsion polymerizing acrylic acid and a non-polyalkenyl polyether difunctional cross-linking agent to a particle size of not more than about 50 μm, preferably not more than about 30 μm, in equivalent spherical diameter. A preferred cross-linking agent is divinyl glycol. It may be desirable to replace up to about 40% by weight of the carboxyl-containing monoethylenically unsaturated monomers by one or more non-carboxyl-containing monoethylenically unsaturated monomers containing only physiologically (and, where appropriate, ophthamologically) innocuous substituents.

The osmotic pressure is preferably achieved by using a physiologically (and, where appropriate, ophthalmologically) acceptable salt in an amount of from about 0.01% to about 1% by weight, based on the total weight of the suspensions. A preferred salt is sodium chloride.

Aminosteroid of formula (XI) may be present in desired therapeutic amount, preferably from about 0.01% to about 10% by weight, based on the total weight of the suspension. Preferred aminosteroids include U-74006, U-74500, U-75412, U-74006F, U-74500A, U-75412A and U-75412-E and aminosteroids of formula I.

In a preferred method of preparing stable sustained release topical ophthalmic delivery systems, the foregoing suspensions are prepared and packaged at the desired viscosity of from 1,000 to about 30,000 centipoises, for administration to the eye in drop form. Upon administration to the eye, viscous gel remains in the eye for a prolonged period of time so as to release in a sustained fashion the aminosteroid entrapped therein.

The present invention thus provides a stable ophthalmic delivery system that not only has the benefits of administration in drop form, but also does not suffer from breakdown limitations due to administration at a viscosity suitable for drops. Through administration at a viscosity such that the suspension can be reliably administered in drop form, but which actually increases when the suspension is so administered, controlled release of aminosteroid medicament is significantly enhanced.

As mentioned above, viscosities substantially over 30,000 cps are generally not suitable for drops; also, viscosities over 100,000 are generally not suitable as ribbons. When the viscosities are substantially lower than 1,000 cps, the ability of the gel to sustain itself after contact with tears is impeded. When a suspension at a pH of from about 3 to about 6.5 and an osmotic pressure of from about 10 to about 400 mOsM contacts the tear fluid, there is an increased gelation with a pH change. As will be appreciated, tear fluid is at a higher pH of about 7.2 to about 7.4. With the pH increase, carboxylic acid (COOH) undergoes a sodium replacement (to COONa), and the sodium form disassociates, causing the polymer to expand.

The relationships between the degree of cross-linking and between the degree of cross-linking and particle size can become quite important variables. Because the particles are present in a suspension, the degree of cross-linking is necessarily high enough to avoid substantial dissolution of the polymer. On the other hand, since rapid gelation is achieved at the time of the pH change, the degree of cross-linking is necessarily low enough to permit gelation. Moreover, if the polymer particle size is too large, induced swelling can tend to fill voids between large particles that are in contact with one another, rather causing gelation.

If the polymer were in a dissolved state, as it would be if there were insufficient cross-linking because the ratio of cross-linker to monomer was too low, particle size would be basically irrelevant. In a suspension, particle size can be relevant to comfort. However, it has been found that in the system of the present invention, the small particle size and light cross-linking synergistically yield rapid gelation to a substantially increased viscosity when the pH changes such as when compositions of the present invention contact tear fluid. In fact, above the 50 μm size this advantage of substantially increased viscosity is not realized. Moreover, at the 50 μm size, there is also reasonably good eye comfort.

In a most preferred form of the invention, the particles are not only subject to the upper size limits described above, but also to a narrow particle size distribution. Such use of a monodispersion of particles, which aids in good particle packing, yields a maximum increased viscosity upon contact of the suspension with the tears and increases eye residence time. At least about 80%, more preferably at least about 90% and most preferably at least about 95%, of the particles should be within a no more than about 10 μm band of major particle size distribution, and overall (i.e., considering particles both within and outside such band) there should be no more than about 20%, preferably no more than about 10% and most preferably no more than about 5% fines (i.e., particles of a size below 1 μm). It is also preferred, as the average particle size is lowered from the upper limit of 50 μm, more preferably 30 μm, to lower sizes such as 6 μm, that the band of major particle size distribution be also narrowed, for example to 5 μm. Preferred sizes for particles within the band of major particle distribution are less than about 30 μm, more preferably less than about 20 μm, most preferably from about 1μm to about 5 μm.

It is apparent that, while the stable sustained delivery systems discussed above are uniquely well-suited to ophthalmic administration, the same systems can be used for topical treatment of skin and mucous membrane by local application to tissue in need of treatment, such as dermal, nasal, vaginal and rectal tissues. However, various features of the systems designed for administration to the eye can be modified in order to produce systems which are even better suited to the contemplated non-ophthalmic route of administration. For example, larger amounts of cross-linking agents and/or higher pH levels may be utilized to provide more viscous gels suited for longer retention on the skin or in body cavities. Furthermore, when it is desired to combine in a single composition the sustained release and prolonged retention properties of the aminosteroid suspensions described above with the immediate release which aminosteroid solutions would provide, or when it is desired to simply achieve the more immediate release and greater penetration possible with solutions, be it for ophthalmic or other route of administration, yet other modifications of the invention can be made as described in more detail hereinbelow.

The exceptional stabilizing effect of lightly-cross-linked carboxy-containing polymers on the aminosteroids of formula (XI) has been demonstrated as follows:

Representative formulations are prepared in accord with EXAMPLE 3 hereinbelow, with the polymer and aminosteroid being as identified in EXAMPLE 3, the concentration of the polymer being 1.0% (w/w) and the concentration of the aminosteroid being either 0.25% or 1.0% (w/w). The stability of the formulation may be monitored by HPLC for each steroid concentration over time, at 5° C., at room temperature, and at 40° C. storage conditions. The 0.25% steroid formulation is observed monthly, over a 3 month period at each temperature, and the 1% steroid formulation is observed over a 3 month period at each temperature. There was essentially no loss of aminosteroid at either concentration level over the two storage conditions. Compared to the known stability of the aminosteroid [Snider et at, *Int. J. Pharm.* 66, 63-70 (1990)], the present formulations stabilize the aminosteriod even at a pH at which the aminosteroid is not ordinarily stable in solution. The improvement in aminosteroid stability may derive from two characteristics of the formulation, i.e. the fact that essentially all of the aminosteroid is suspended in the solid form and the fact that the polymer and aminosteroid interact in a way that protects the aminosteroid from degradation.

The changes in rheological properties of the polymer also indicate that such interaction occurs in the presence of aminosteroid. In steady state shear experiments, a placebo formulation displays a zero shear rate viscosity, lower than when the representative aminosteroid identified in EXAMPLE 3 is present at either 0.5% or 1.0%. The results indicate that the aminosteroid interacts with the representative polymer specified in EXAMPLE 3 to provide a stronger polymer network structure than for the polymer alone. Moreover, strain sweep and frequency sweep experiments demonstrate a more viscoelastic and complex viscosity, supporting the evidence of a stronger network structure for formulations in which the aminosteroid is present.

The viscosity of 1.0% w/w aminosteroid formulations prepared according to EXAMPLE 3 below, but with varying concentrations of polymer (0.25% to 1.0% w/w), may be compared with that of corresponding formulations lacking the aminosteroid component. Viscosity is measured by a Brookfield LTV spindle type viscometer with spindle #25, 12 rpm. Viscosity increases with increasing concentrations of the polymer in both types of formulations (i.e. with and without aminosteriod). However, the aminosteroid-containing formulations consistently displays significantly higher viscosities than the corresponding formulations without aminosteroids across the entire range that is tested. When the concentration of aminosteroid is varied (from 0.1 to 1.0% w/w) while the concentration of polymer is maintained constant (at 1.0% w/w), a concentration viscosity dependence is established for the aminosteroid. However, when the steroid fluorometholone is added to the polymer vehicle at either the 0.1% or 1.0% w/w level, no significant change in viscosity is observed. While fluorometholone, which is not an aminosteroid, is also suspended in the polymer vehicle, it appeared not to interact with the polymer. In other words, fluorometholone acts as a non-interactive filler while the representative aminosteroid acts as an interactive filler. The interaction between aminosteroid and polymer in these experiments is further substantiated by the fact that the pH at which the aminosteroid was added to the formulation appeared to affect the degree of interaction. When the pH is lower than 6.0, the aminosteroid is highly ionized and the interaction becomes so strong that agglomeration is seen. This pH dependent interaction also suggests an ionic interaction between aminosteroid and polymer.

As noted hereinabove, the stable compositions obtained in accord with the foregoing detailed description provide for sustained release of the aminosteroid, by virtue of the fact that the aminosteroid is in suspension. Prolonged retention at the site of application can also be readily provided by these compositions by virtue of their viscosity.

The aminosteroids of formula XI are useful in the treatment of a variety of medical conditions in warm-blooded animals, including humans. The present invention provides pharmaceutical compositions for administration in the treatment or prevention of the various conditions for which the aminosteroids are known to be useful, e.g. from International Publication No. WO 87/01706, and from parent application Ser. No. 07/933,574, grandparent Ser. No. 07/838,875 and great grandparent application Ser. No. 07/537,062, now U.S. Pat. No. 5,124,154. Briefly, such conditions include spinal trauma; head injury (mild, moderate or severe); subarachnoid hemorrhage (including the associated cerebral vasospasm); skin graft rejection; ischemic stroke; excessive mucous secretion; asthma; muscular dystrophy; shock (hemorrhagic, septic or traumatic); cardiac toxicity induced by anti-cancer agents such as adriamycin; Parkinsonism, Alzheimer's disease and other neurological disorders of a degenerative nature; severe burns; ARDS; multiple sclerosis; organ damage occurring during reperfusion following transplant; osteoarthritis, rheumatoid arthritis and other inflammatory diseases; dermatological disorders such as inflammation and psoriasis; immunological nephrotic syndrome; allergic reactions; systemic lupus erythematosis; atherosclerosis; emphysema; metastases and tumor growth; cluster headaches, ulcers induced by stress; complications from radiation damage, brain tumors and damage after myocardial infarction; and burns and wounds (to promote healing). The aminosteroids are further known to be useful in the prevention of damage following cardiopulmonary resuscitation, cardiac infarction and neurological or cardiovascular surgery; in the treatment and prevention of many of the conditions for which glucocorticoid pharmaceuticals are known to be useful (some of which are listed hereinabove); in the treatment or prevention of ophthalmic diseases or disorders such as cataracts, glaucoma or the risk of glaucoma associated with significantly elevated intraocular pressure, inflammatory eye disease, retinal eye disease, intraocular pressure rise due to uveitis, post-infarct ambolus, traumatic eye injury (such as blunt trauma, compression injury, hyphema, surgical trauma, etc.), neovascular or ischemic eye disease (conditions in the eye involving ischemia such as corneal edema from prolonged wearing of contact lenses and the like), bullous keratitis, dry eye including keratitis sicca, alkali burn and conditions arising from transplantation of ocular cells.

The foregoing is not meant to imply that each of the aminosteroids of formula XI is useful for every condition noted above. However, one skilled in the art can readily ascertain which steroids are useful for which purposes, for example, using assay procedures referred to in International Publication No. WO 87/01706.

Routes of administration, frequency of administration and dosage levels vary with the particular aminosteroid selected, condition being treated, severity of the condition, size, weight and age of the patient and other well-known factors. Typical dosage ranges include from about 0.05 to about 100 mg/kg/day, one to four times daily, by various routes, e.g. orally, parenterally (for example, intramuscularly), nasally, rectally, by inhalation, topically (e.g. dermally, ophthalmically, or vaginally) or by intraocular injection. In addition to selecting the route of administration most suitable to a particular condition, the method of stabilizing the aminosteroid and the resultant stable compositions will be selected which will be most appropriate for the condition and route of administration. The polymer-containing suspensions, for example, are particularly suitable for topical (e.g., ophthalmic, dermal or vaginal), intraocular, nasal and rectal administration. Obviously, however, the suspension and solutions can be administered by other routes as well.

Topical administration to the skin is generally preferred for the treatment of many dermatological conditions, particularly skin inflammation and psoriasis, but particularly serious dermal conditions may require systemic administration, alone or in conjunction with topical treatment.

In the case of ophthalmic conditions, topical administration is preferable when the target of the treatment is located in or near the anterior chamber of the eye. By contrast, because the flow of aqueous humor is from the ciliary body (behind the iris) forward towards the cornea before it exits through the trabecular meshwork and Schlemm's canal, penetration of drugs to the back of the eye when administered topically to the front of the eye occurs with some difficulty. It is therefore often more effective to administer drugs intended for the treatment of uveal and retinal diseases by the systemic route where access to the eye occurs through the choroid plexus, or by the intravitreal route. Some of the more severe eye diseases affect those targets which are difficult to treat effectively by the topical route and they can be associated with markedly impaired vision or blindness. Accordingly, the topical route is preferred for convenience of individual patient self-administration, and the intraocular and systemic routes are preferred for surgical and presurgical administration.

In order to maintain an ocularly adequate therapeutic level of drug in the back of the eye where surgery is not involved, or has been concluded, the present invention also contemplates the treatment of an ophthalmic disease by administration of a therapeutically effective amount of amino-substituted steroid antioxidant agent (including salts, hydrates or solvates), by oral or intramuscular routes, in addition to the convenient topical route or by intraocular injection.

Aqueous solutions, aqueous suspensions, ointments, and gels are preferably used for topical formulations, e.g. for ophthalmic or dermal administration. The aqueous formulations may also contain liposomes for creating a reservoir of dissolved amino-substituted steroid therapeutic agent for contact with the tear film. Particularly preferred among topical formulations are gels, which enhance pre-corneal retention and protect the amino-substituted steroids from degradation without the inconvenience and impairment of vision associated with ointments.

Topical formulations should generally include between 0.01 and 10% by weight, preferably between 0.1 and 5% by weight, of the amino-substituted steroid therapeutic agent, together with the amount of polymer in an aqueous medium.

Other additives which are desirably included in the topical formulations include sodium chloride, EDTA (disodium edetate), pH adjusters, buffers, surfactants, and preservatives like BAK (benzalkonium chloride). Administration of the formulation to the eye or skin will typically be carried out between one and four times a day, depending on the particular problem being treated.

Formulations for ocular injection, intramuscular injection, oral administration and other routes can be formulated in accord with techniques well-known to those skilled in the art of pharmaceutical formulations. The amounts of aminosteroid, and polymer are included in an aqueous medium; as in the case of topical formulations, other additives may be included just so long as they do not interfere with the stabilization and are appropriate for the selected route of administration. See, for example applicants' parent, grandparent and great grandparent applications referenced hereinabove, and *Remington's Pharmaceutical Sciences*, seventeenth edition, ed. Alfonso R. Gennaro, Mack Publishing Company, Easton, Pa. (1985).

The following examples are given for illustrative purposes only and should in no way be construed as limiting the subject matter presently disclosed and claimed.

EXAMPLE 1

Bioadhesive compositions of matter are prepared containing U-74006F, U-74500A or U-75412A suitable for topical administration to the eye. A formulation of 5,000 cps viscosity or greater is prepared by suspending 1 g of NOVEON AA-1, a polycarbophil, in 95 g of intravenous grade water. The solution is mixed by overhead stirring for 1 hour. To this solution 0.5 g of sodium chloride and 0.1 g of EDTA are added and stirring is continued for 5 minutes. The pH of the solution is adjusted to 6.0 by dropwise addition of 1N sodium hydroxide. This forms a gel. This composition is sterilized at 121° C. for 30 minutes. To this formulation is added 0.15 g of the aminosteroid therapeutic agent disolved in 6.0N HCL by sterile filtration and stirring is continued for 30 minutes. The total weight is adjusted to 100 g by addition of water by sterile filtration. This formulation is then aseptically filled into unit dose containers and applied topically. Thus, to prevent or treat an ophthalmic disease or disorder, the composition is topically administered to the eye one to four times a day, with the aminosteroid therapeutic agent being introduced in an ophthalmically effective amount to arrest processes damaging to the eye (particularly oxidation processes) of a human or other animal that is subject to intraocular damage and in need of improved visual function or prevention of its loss from such damage.

EXAMPLE 2

Compositions similar to those of EXAMPLE 1 are prepared by following the procedure of EXAMPLE 1, but adding 100 mg of the preservative benzalkonium chloride prior to sterilization. There is produced a preserved formulation suitable for sterile filling into multidose containers. The formulation is applied topically as in EXAMPLE 1.

EXAMPLE 3

A 100 g batch of pharmaceutical composition is prepared as described below:

| INGREDIENT | CONCENTRATION (% w/w) |
|---|---|
| Aminosteroid U-74006F | 1.0% |
| Polycarbophil 976 (Noveon AA-1) | 1.0% |
| Sodium Chloride | 0.5% |
| EDTA | 0.1% |
| Hydrochloric Acid, 0.2N | 10.0% |
| Sodium Hydroxide, 2N | to adjust pH |
| Water, q.s. to | 100% |

The polymer (1.0 g) is slowly dispersed in approximately 75 g of sterile water for injection and stirred for 1 hour at 400 rpm. Then, 0.1 g of EDTA is added to the polymer mixture and stirred for 15 minutes. Sodium chloride (0.5 g) is added and stirring is continued for 15 minutes. The polymer mixture is autoclaved for 45 minutes at 121° C., then cooled to room temperature. The pH is adjusted to approximately 6.2 by addition of 2N aqueous sodium hydroxide solution through a sterile filter. In a 100 mL beaker, the aminosteroid (1.0 g) is dissolved in 10 g of 0.2N aqueous hydrochloric acid. While stirring the polymer mixture, the aminosteroid mixture is added thereto slowly, in a drop-wise fashion, through a sterile filter. The pH of the resultant mixture is adjusted to approximately 7.2 with 2N aqueous sodium hydroxide solution. The final weight of the formulation is adjusted to 100 g with sterile water for injection and the formulation is sealed under a blanket of filtered nitrogen. The resultant composition has a physiological pH with a slightly hypotonic osmolality. The viscosity of the formulation is approximately 30,000 cps.

The resultant composition is of particular interest for topical treatment of ophthalmic conditions.

EXAMPLE 4

A 100 g batch of pharmaceutical composition is prepared as described below:

| INGREDIENT | CONCENTRATION (% w/w) |
|---|---|
| Aminosteroid U-74006F | 1.0% |
| CARBOPOL 974P | 1.0% |
| Sodium Chloride | 0.5% |
| EDTA | 0.1% |
| Hydrochloric Acid, 0.2N | 10.0% |
| Sodium Hydroxide, 2N | to adjust pH |
| Water, q.s. to | 100% |

CARBOPOL 974P (1.0 g) is slowly dispersed in approximately 75 g of sterile water for injection and stirred for one hour at 400 rpm, using an overhead stirrer. Then 0.1 g of EDTA is added to the polymer mixture and stirred for 15 minutes. Sodium chloride (0.5 g) is added and stirring is continued for 15 minutes. The mixture is autoclaved at 121° C. for 15 to 30 minutes to achieve sterilization, then cooled to room temperature. The pH is adjusted to approximately 6.2 by addition of 2N aqueous sodium hydroxide solution through a sterile filter. In a 100 mL beaker, the aminosteroid (1.0 g) is dissolved in 10 g of 0.2N HCl. While stirring the polymer mixture, the aminosteroid is added slowly, in a drop-wise manner, through a sterile filter. Finally, the pH is adjusted to 7.2 with 2N NaOH and the final weight of the formulation is brought to 100 g by addition of sterile water for injection through a sterile filter.

A 1% suspension prepared in this manner is of particular interest for the topical treatment of dermal conditions.

EXAMPLE 5

The foregoing examples can be repeated, substituting or adding one or more other aminosteroid therapeutic agents selected from the $C_{20}$ through $C_{26}$ aminosteroids of the formula XI structure (especially those which exhibit antioxidant functions), and pharmaceutically acceptable salts, hydrates, or solvates thereof, keeping the total amount of agent as in EXAMPLES 1-6. One such agent is U-77372E. The structure of U-77372E, 21-[4-(4,6-bis-(2-pyridinyl)triazin-2-yl)- 1-piperazinyl]-16α-methylpregna-1,4,9(11)-triene-3,20-dione methanesulfonate, may be obtained from the description in Braughler et al, *Biochemical Pharmacology* 37:3856 (1988).

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A topical opthalmic composition comprising:
   (a) from about 0.01 to about 10% by weight of at: amino-substituted steroid therapeutic agent selected from the group consisting of the $C_{20}$ through $C_{26}$ aminosteroids of the formula XI

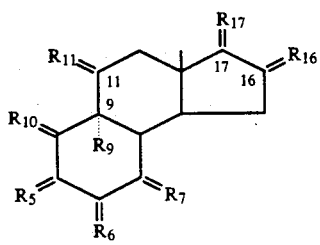 (XI)

where:
(A-I) $R_6$ is $\alpha$-$R_{61}$:$\beta$-$R_{62}$, $R_{10}$ is $\alpha$-$R_{101}$:$\beta$-$R_{102}$ and $R_7$ is $\alpha$-H: $\beta$-H, where one of $R_{61}$ and $R_{62}$ is —H, and the other is —H, —F, or $C_1$-$C_3$ alkyl, $R_{102}$ is —$CH_3$, $R_{101}$ and $R_5$ taken together are —($CH_2$)$_2$—C(—$R_{33}$)—CH= or —CH—CH—CO—CH=, where $R_{33}$ is =O or $\alpha$-H: $\beta$-O$R_{34}$ or $\alpha$-O$R_{34}$: $\beta$-H, where $R_{34}$ is —H, —P(=O)(OH)$_2$, —CO—$CH_3$, —CO—$C_2H_5$, —CO—$C_6H_5$, —CO—O—$CH_3$ or —CO—O—$C_2H_5$;

(A-II) $R_5$ is $\alpha$-$R_{53}$:$\beta$-$R_{54}$, $R_6$ is $\alpha$-$R_{63}$:$\beta$-$R_{64}$, $R_{10}$ is $\alpha$-$R_{103}$: $\beta$-$R_{104}$ and $R_7$ is $\alpha$-H: $\beta$-H, where one of $R_{63}$ and $R_{64}$ is —H, and the other taken together with one of $R_{53}$ and $R_{54}$ forms a second bond between $C_5$ and $C_6$,$R_{104}$ is —$CH_3$, $R_{103}$ and the other of $R_{53}$ and $R_{54}$ taken together are —($CH_2$)$_2$—C(H)(OH)—$CH_2$— or —($CH_2$)$_2$—C[H][OP(=O)—(OH)$_2$]—$CH_2$—

(A-III) $R_{10}$ and $R_5$ taken together are =CH—CH=C(O$R_3$)—CH= where $R_3$ is —H, —P(=O)(OH)$_2$, $C_1$-$C_3$-alkyl, —CO—H, $C_2$-$C_4$ alkanoyl or benzyl, $R_6$ is $\alpha$-$R_{65}$:$\beta$-$R_{66}$ where one of $R_{65}$ and $R_{66}$ is —H, and the other is —H, —F, or $C_1$-$C_3$ and $R_7$ is $\alpha$-H: $\beta$-H;

(A-IV) $R_5$ is $\alpha$-$R_{57}$:$\beta$-$R_{58}$, $R_6$ is $\alpha$-$R_{67}$:$\beta$-$R_{68}$, $R_7$ is $\alpha$-H: $\beta$-H and $R_{10}$ is $\alpha$-$R_{107}$:$\beta$-$R_{108}$, where one of $R_{57}$ and $R_{58}$ is —H, $R_{107}$ and the other of $R_{57}$ and $R_{58}$ taken together are —($CH_2$)$_2$—C(=$R_{33}$)—$CH_2$, where $R_{33}$ is as defined above, $R_{108}$ is —$CH_3$, where one of $R_{67}$ and $R_{68}$ is —H and the other is —H, —F, or $C_1$-$C_3$ alkyl;

(A-V) $R_6$ is $R_{69}$:$R_{610}$, $R_7$ is $R_{79}$:$R_{710}$, $R_{10}$ is $\alpha$-$R_{109}$:$R_{1010}$, where one of $R_{69}$ and $R_{610}$ is —H and the other taken together with one of $R_{79}$ and $R_{710}$ forms a second bond between $C_6$ and $C_7$, and the other of $R_{79}$ and $R_{710}$ is —H, $R_{1010}$ is —$CH_3$, $R_{109}$ and $R_5$ taken together are —($CH_2$)$_2$—C(=$R_{33}$)—CH= or —CH=CH—CO—CH=, where $R_{33}$ is as defined above; where:

(C-I) $R_{11}$ is $\alpha$-$R_{111}$:$\beta$-$R_{112}$, where one of $R_{111}$ and $R_{112}$ is taken together with $R_9$ to form a second bond between $C_9$ and $C_{11}$ and the other of $R_{111}$ and $R_{112}$ is —H;

(C-II) $R_9$ is —Cl and $R_{11}$ is =O or $\alpha$-H:$\beta$-$R_{114}$ where $R_{114}$ is —Cl or —OH;

(C-III) $R_9$ is —H or —F and $R_{11}$ is =O or $\alpha$-$R_{115}$:$\beta$-$R_{116}$, where one of $R_{115}$ and $R_{116}$ is —H, and the other of $R_{115}$ and $R_{116}$ is —H, —OH or $C_1$-$C_{12}$ alkoxy;

(C-IV) $R_9$ is —H or —F and $R_{11}$ is $\alpha$-O—CO—$R_{117}$: $\beta$-H, where $R_{117}$ is (A) $C_1$-$C_3$ alkyl,
(B) $C_1$-$C_{12}$ alkoxy,
(C) furanyl,
(D) —N$R_{122}R_{123}$, where one of $R_{122}$ and $R_{123}$ is —H, methyl or ethyl and the other is —H, $C_1$-$C_4$ alkyl or phenyl,
(E) —$X_3$—$X_1$, where $X_3$ is —O— or a valence bond, where $X_1$ is phenyl optionally substituted with 1 through 2 —Cl, —Br, $C_1$-$C_3$ alkoxy, —COOH, —$NH_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino and —NH— CHO or with 1 —F or —$CF_3$;

where:
(D-I) $R_{16}$ is $R_{161}$:$R_{162}$ and $R_{17}$ is $R_{171}$:$R_{172}$, where one of $R_{161}$ and $R_{162}$ is —H or —$CH_3$ and the other taken together with one of $R_{171}$ and $R_{172}$ forms a second bond between $C_{16}$ and $C_{17}$, and the other of $R_{171}$ and $R_{172}$ is —C(=Z)—($CH_2$)$_n$—N$R_{21}R_{210}$, where Z is =O, =$CH_2$ or $R_{179}$:—H where $R_{179}$ is —H or —$CH_3$, where n is 0 through 6, where (A) $R_{21}$ is
   (1) —($CH_2$)$_m$—N$R_{211}$—$X_2$, where m is 2, 3 or 4, where $R_{211}$ is —H or $C_1$-$C_3$ alkyl, where $X_2$ is:
   [A]
   (a) pyridin-2-, 3- or 4-yl or the N-oxide thereof optionally substituted by 1 or 2 $R_{212}$, being the same or different, where $R_{212}$ is
      (i) —F,
      (ii) —Cl,
      (iii) —Br,
      (iv) $C_1$-$C_5$ alkyl,
      (v) —$CH_2$—CH=$CH_2$,
      (vi) —$X_1$, where $X_1$ is as defined above,
      (vii) —N$R_{213}R_{213}$ where the $R_{213}$'s are the same or different and are —H, $C_1$-$C_3$ alkyl or —$CH_2$—CH=$CH_2$,
      (viiiα) *$CH_2$—($CH_2$)$_q$—$CH_2$—N*— where the atoms marked with an asterisk (*) are bonded to each other resulting in the formation of a ring, where q is 1 through 5,
      (viiiβ) *$CH_2$—$CH_2$—($CH_2$)$_c$—G—($CH_2$)$_d$—$CH_2$—$CH_2$—N*— where the atoms marked with an asterisk (*) are bonded to each other resulting in the formation of a ring, where G is —O—, —S—, —SO—, —$SO_2$— or —NH$R_{214}$, where $R_{214}$ is —H, $C_1$-$C_3$ alkyl, or $X_1$ as defined above, where c and d are the same or different and are 0 through 2 with the proviso that the total number of ring carbon atoms is 4, 5 or 6, [a]
      (ix) 3-pyrrolin-1-yl, [b]
      (x) pyrrol-1-yl optionally substituted with $C_1$-$C_3$ alkyl, [c]
      (xi) piperidin-1-yl optionally substituted with 1 or 2 $C_1$-$C_3$ alkyl, [d]
      (xii) 1,2,3,6-tetrahydro-pyridin-1-yl, [e]
      (xiii) 1-hexamethyleneimino containing a 3- or 4- double bond or 3- and 5-double bonds, [f]

(xiv) 1,4-dihydro-1-pyridinyl substituted in the 4 position by two $C_1$-$C_3$ alkyl being the same or different, [g]

(xv) —OH, (xvi) $C_1$-$C_3$ alkoxy, (xvii) —$NR_{217}$—$(CH_2)_e$—Q where Q is 2-pyridinyl where $R_{217}$ is —H or $C_1$-$C_3$ alkyl and e is 0 through 3 (1)

(xviii) pyridin-2-, 3- or 4-yl, (b) 1,3,5-triazin-4-yl or the N-oxide thereof optionally substituted at the 2- and/or 6-position with $R_{212}$ as is defined above, (4)

(c) pyrimidin-4-yl or the N-oxide thereof optionally substituted at the 2- and/or 6-position with $R_{212}$ as is defined above, (5)

(d) pyrimidin-2-yl optionally substituted at the 4- and/or 6-position with 1 or 2 $R_{212}$ as is defined above, (6)

(e) pyrazin-2-yl optionally substituted with 1 or 2 $R_{212}$ as is defined above, (7)

(f) imidazol-2-yl optionally substituted in the 1 position with $C_1$-$C_3$ alkyl or —$X_1$, where $X_1$ is as defined above, and further optionally substituted with 1 or 2 $R_{212}$ as defined above, (8)

(g) 1,3,4-triazol-2-yl optionally substituted in the 1 position with $C_1$-$C_3$ alkyl or —$X_1$, where $X_1$ is as defined above, and further optionally substituted with $R_{212}$ as defined above, (9)

(h) imidazol-4- or 5-yl optionally substituted in the 1 position with $C_1$-$C_3$ alkyl or —$X_1$, where $X_1$ is as defined above, and further optionally substituted with 1 or 2 $R_{212}$ as defined above, (10)

(i) benzo[b]thien-2-yl, (12a)

(j) indol-2-yl, (12b)

(k) benzo[b]thiazol-2-yl, (12c)

(l) benzimidazol-2-yl, (12d)

(m) 4-[2-[4-[2,6-bis(1-pyrrolidinyl)-4-pyrimidinyl]-1-piperazinyl]ethyl]piperazinyl, (13)

(n) 1,2,4-triazin-3-yl optionally substituted at the 5- and/or 6-position with $R_{212}$ as is defined above, (14)

(2) (1-piperazinyl)-$(C_2$-$C_4)$alkyl optionally substituted in the 4-position with —$X_1$ or —$X_2$ as defined above, [B]

(3) —$X_2$, as defined above, [O]

(4) —$(CH_2)_m$—$X_4$ where m is as defined above and where $X_4$ is (a) —O—$CH_2CH_2$—Y, where Y is $C_1$-$C_3$ alkylamino, di$(C_1$-$C_3)$alkylamino where the alkyl groups are the same or different, $C_3$-$C_6$alkyleneimino, optionally substituted with 1 or 2 $C_1$-$C_3$ alkyl, (b) —$NR_{220}CH_2CH_2$—Y, where $R_{220}$ is —H or $C_1$-$C_3$ alkyl and Y is as defined above, (c) —$(CH_2)_g$—$N(R_{220})$—$X_2$, where g is 2, 3 or 4, and where $R_{220}$ and $X_2$ are as defined above, [H]

(5) —$(CH_2)_m$—$NR_{222}R_{223}$, where $R_{222}$ is —H or $C_1$-$C_3$ alkyl and $R_{223}$ is —$X_1$ or —$X_2$ as defined above, or $R_{222}$ and $R_{223}$ are taken together with the attached nitrogen atom to form a saturated mono-nitrogen $C_3$-$C_6$ heterocyclic ring and where m is as defined above, [I]

(6) —$(CHCH_3)_b$—$(CH_2)_f$—$R_{224}$, where b is 0 and f is 1 through 3 or b is one and f is 0 through 3, where $R_{224}$ is phenyl substituted with 1 through 3 —OH, $C_1$-$C_3$ alkoxy, —$NR_{225}R_{226}$ where $R_{225}$ and $R_{226}$ are the same or different and are —H, $C_1$-$C_3$ alkyl or are taken together with the attached nitrogen atom to form a $C_4$-$C_7$ cyclic amino ring, [J]

(7) —$(CH_2)_i$—$X_2$, where i is 1 through 4 and $X_2$ is as defined above, [K]

(8) (1-piperazinyl)acetyl substituted in the 4-position by $X_2$ where $X_2$ is as defined above, [L]

(9) (1-piperazinyl)carbonylmethyl substituted in the 4-position by —$X_2$ where $X_2$ is as defined above, and [M]45-152

(B) $R_{210}$ is (1) —H, (2) $C_1$-$C_3$ alkyl, (3) $C_5$-$C_7$ cycloalkyl, (4) —$(CH_2)_m$—$NR_{211}$—$X_2$, where m, $R_{211}$ and $X_2$ are as defined above, [A]

(5) (1-piperazinyl)-$(C_2$-$C_4)$alkyl optionally substituted in the 4-position with —$X_1$ or —$X_2$ as defined above, [B]

(6) —$(CH_2)_m$—$X_4$, where m and $X_4$ are as defined above, [H]

(7) —$(CH_2)_m$—$NR_{222}R_{223}$, where m, $R_{222}$ and $R_{223}$ are as defined above, [I]

(8) —$(CHCH_3)_b$—$(CH_2)_f$—$R_{224}$, where b, f and $R_{224}$ are as defined above, [J]

(C) $R_{21}$ and $R_{210}$ are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, [C-1]

(2) 2-(carboxy)-1-piperidinyl optionally as the $C_1$-$C_3$ alkyl ester or as a pharmaceutically acceptable salt, [C-2]

(3) 2-(carboxy)-1-hexamethyleneimino optionally as the $C_1$-$C_3$ alkyl ester or as a pharmaceutically acceptable salt, [C-3]

(4) 2-(carboxy)-1-heptamethylene-imino optionally as the $C_1$-$C_3$ alkyl ester or as a pharmaceutically acceptable salt, [C-4]

(5) 1-piperazinyl substituted in the 4-position with $R_{228}$—CO—$(CH_2)_j$— where $R_{228}$ is —$X_1$, —$NR_{229}X_1$ or 2-furanyl, where $R_{229}$ is —H or $C_1$-$C_3$ alkyl, where j is 0 through 3 and $X_1$ is as defined above, [D]

(6) 1-piperazinyl substituted in the 4-position with $X_2$—$(CH_2)_j$—, where $X_2$ and j are as defined above, [E]

(7) 1-piperazinyl substituted in the 4-position with $X_1$—$(CH_2)_j$—, where $X_1$ and j are as defined above, [F]

(8) 4-hydroxy-1-piperidinyl substituted in the 4-position with $X_1$ as defined above, [G]

(9) 1-piperazinyl substituted in the 4-position with $X_2$—$NR_{229}$—CO—$(CH_2)_i$—, where $X_2$, $R_{229}$ and i are as defined above; [N]

(D-II) $R_{16}$ is $\alpha$-$R_{163}$:$\beta$-$R_{164}$ where one of $R_{163}$ and $R_{164}$ is —H and the other is —H, —F, —$CH_3$ or —OH, and $R_{17}$ is —CH—$(CH_2)_p$—$NR_{21}R_{210}$, where p is 1 or 2, where $R_{21}$ and $R_{210}$ are as defined above;

(D-III) $R_{16}$ is $\alpha$-$R_{165}$:$\beta$-$R_{166}$ and $R_{17}$ is $\alpha$-$R_{175}$:$\beta$-$R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2CH_7$, alkanoyloxy or —O—CO—$X_1$, where $X_1$ is as defined above, and where $R_{176}$ is —C(=Z)—($CH_2$)n—$NR_{21}R_{210}$, where Z, n, $R_{21}$ and $R_{210}$ are as defined above;

(D-IV) the 16,17-acetonide of a compound where $R_{165}$ is —OH, $R_{166}$ is —H, $R_{175}$ is —OH and $R_{176}$ is —C(=Z)—($CH_2$)$_n$—$NR_{21}R_{210}$, where Z, n, —$R_{21}$ and $R_{210}$ are as defined above;

and the pharmaceutically acceptable salts, hydrates and solvates thereof;

with the following overall provisos that:

(I) one of $R_{161}$ or $R_{162}$ is taken together with one of $R_{171}$ or $R_{172}$ to form a second bond between $C_{16}$ and $C_{17}$, only when $R_{10}$ is $\alpha$-$R_{101}$:$\beta$-$R_{102}$, $\alpha$-$R_{103}$:$\beta$-$R_{104}$ $\alpha$-$R_{107}$:$\beta$-$R_{108}$ or $\alpha$-$R_{109}$:$\beta$-$R_{1010}$, (II) $R_{17}$ is —CH—($CH_2$)$_p$—$NR_{21}R_{210}$, only when $R_{10}$ is $\alpha$-$R_{101}$:$\beta$-$R_{102}$, a-$R_{103}$:$\beta$-$R_{104}$, $\alpha$-$R_{107}$: $\beta$-$R_{108}$ or $\alpha$-$R_{109}$:$\beta$-$R_{1010}$, (III) $R_5$ and $R_{10}$ taken together are =CH—CH=C($OR_3$)—CH=, only when $R_{17}$ is $\alpha$-$R_{175}$:$\beta$-$R_{176}$ or the 16,17-acetonide of a compound where $R_{16}$ is $\alpha$-OH: $\beta$-H and $R_{17}$ is $\alpha$-OH: $\beta$-C(=Z)—($CH_2$)$_n$—$NR_{21}R_{210}$, and (IV) $R_5$ is $\alpha$-$R_{57}$:$\beta$-$R_{58}$, only when $R_{17}$ is $\alpha$-$R_{175}$:$\beta$-$R_{176}$ or $\alpha$-OH: $\beta$-C—(=Z)—($CH_2$)$_n$—$NR_{21}R_{210}$, or the 16,17-acetonide thereof; and (b) an opthalmically acceptable carrier therefor comprising lightly cross-linked carboxy-containing polymer and water.

2. The composition according to claim 1, comprising from about 0.1 to about 5% by weight of said therapeutic agent.

3. The composition according to claim 1, wherein said polymer is polycarbophil.

4. The composition according to claim 3, wherein said polycarbophil is a suspension-polymerized acrylic acid and divinyl glycol AA-1.

5. The composition according to claim 1, wherein the lightly cross-linked carboxy-containing polymer is a polyalkenyl polyether, lightly crosslinked carboxy-containing polymer.

6. The composition according to claim 1, further comprising one or more additives selected from the group consisting of sodium chloride, disodium edetate, suffactants and preservatives.

7. The composition according to claim 1, further comprising sodium chloride.

8. The composition according to claim 1, further comprising disodium edetate.

9. The composition according to claim 1, further comprising a suffactant.

10. The composition according to claim 1, further comprising a preservative.

11. The composition according to claim 10, wherein the preservative is benzalkonium chloride.

12. The composition according to claim 1, wherein the therapeutic agent is selected from the group consisting of 21-[4-(2,6-dipyrrolidinyl-4-pyrimidinyl)-1-piperazinyl]-16$\alpha$-methylpregna-1,4,9(11)-triene-3,20-dione, or a pharmaceutically acceptable salt, hydrate or solvate thereof; 21-[4-[5,6-bis(diethylamino)-2-pyridinyl]-1-piperazinyl]-16$\alpha$-methylpregna-1,4,9(11)-triene-3,20-dione, or a pharmaceutically acceptable salt, hydrate or solvate thereof; and 21-[4-(3-ethylamino-2-pyridinyl)-1-piperazinyl]-16$\alpha$-methylpregna-1,4,9(11)-triene-3,20-dione, or a pharmaceutically acceptable salt, hydrate or solvate thereof.

13. The composition according to claim 12, wherein the therapeutic agent is selected from the group consisting of the methanesulfonate salt of 21-[4-(2,6-dipyrrolidinyl-4-pyrimidinyl)-1-piperazinyl]-16$\alpha$-methylpregna-1,4,9(11)-triene-3,20-dione; the hydrochloride salt of 21-[4-[5,6-bis(diethylamino)-2-pyridinyl]-1-piperazinyl]-16$\alpha$-methylpregna-1,4,9(11)-triene-3,20-dione; and the hydrochloride or maleic acid salt of 21-[4-(3-ethylamino-2-pyridinyl)-1-piperazinyl]-16$\alpha$-methylpregna-1,4,9(11)-triene-3,20-dione.

14. A pharmaceutical composition for oral administration comprising:

(a) from about 0.05 to about 5% by weight of an amino-substituted steroid therapeutic agent selected from the group consisting of the $C_{20}$ through $C_{26}$ aminosteroids of the formula XI

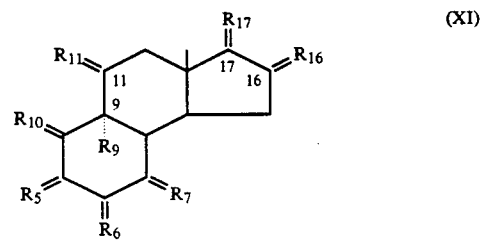

(XI)

where:

(A-I) $R_6$ is $\alpha$-$R_{61}$:$\beta$-$R_{62}$, $R_{10}$ is $\alpha$-$R_{101}$:$\beta$-$R_{102}$ and $R_7$ is $\alpha$-H: $\beta$-H, where one of $R_{61}$ and $R_{62}$ is —H, and the other is —H, —F, or $C_1$-$C_3$ alkyl, $R_{102}$ is —$CH_3$, $R_{101}$ and $R_5$ taken together are —($CH_2$)$_2$—C(—$R_{33}$)—CH= or —CH—CH—CO—CH=, where $R_{33}$ is =O or $\alpha$-H: $\beta$-$OR_{34}$ or $\alpha$-$OR_{34}$: $\beta$-H, where $R_{34}$ is —H, —P(=O)(OH)$_2$, —CO—$CH_3$, —CO—$C_2H_5$, —CO—$C_6H_5$, —CO—O—$CH_3$ or —CO—O—$C_2H_5$;

(A-II) $R_5$ is $\alpha$-$R_{53}$:$\beta$-$R_{54}$, $R_6$ is $\alpha$-$R_{63}$:$\beta$-$R_{64}$, $R_{10}$ is $\alpha$-$R_{103}$: $\beta$-$R_{104}$ and $R_7$ is $\alpha$-H: $\beta$-H, where one of $R_{63}$ and $R_{64}$ is —H, and the other taken together with one of $R_{53}$ and $R_{54}$ forms a second bond between $C_5$ and $C_6$, $R_{104}$ is —$CH_3$, $R_{103}$ and the other of $R_{53}$ and $R_{54}$ taken together are —($CH_2$)$_2$—C(H)(OH)—$CH_2$— or —($CH_2$)$_2$—C[H][OP(=O)—(OH)$_2$]—$CH_2$—

(A-III) $R_{10}$ and $R_5$ taken together are =CH—CH=C($OR_3$)—CH= where $R_3$ is —H, —P(=O)(OH)$_2$, $C_1$-$C_3$ alkyl, —CO—H, $C_2$-$C_4$ alkanoyl or benzyl, $R_6$ is $\alpha$-$R_{65}$:$\beta$-$R_{66}$ where one of $R_{65}$ and $R_{66}$ is —H, and the other is —H, —F, or $C_1$-$C_3$ alkyl and $R_7$ is $\alpha$-H: $\beta$-H;

(A-IV) $R_5$ is $\alpha$-$R_{57}$:$\beta$-$R_{58}$, $R_6$ is $\alpha$-$R_{67}$:$\beta$-$R_{68}$, $R_7$ is $\alpha$-H: $\beta$-H and $R_{10}$ is $\alpha$-$R_{107}$:$\beta$-$R_{108}$, where one of $R_{57}$ and $R_{58}$ is —H, $R_{107}$ and the other of $R_{57}$ and $R_{58}$ taken together are —($CH_2$)$_2$—C(=$R_{33}$)—$CH_2$, where $R_{33}$ is as defined above, $R_{108}$ is —$CH_3$, where one of $R_{67}$ and $R_{68}$ is —H and the other is —H, —F, or $C_1$-$C_3$ alkyl;

(A-V) $R_6$ is $R_{69}$:$R_{610}$, $R_7$ is $R_{79}$:$R_{710}$, $R_{10}$ is $\alpha$-$R_{109}$:$R_{1010}$, where one of $R_{69}$ and $R_{610}$ is —H and the other taken together with one of $R_{79}$ and $R_{710}$ forms a second bond between $C_6$ and $C_7$, and the other of $R_{79}$ and $R_{710}$ is —H, $R_{1010}$ is —$CH_3$, $R_{109}$ and $R_5$ taken together are —($CH_2$)$_2$—C(50 $R_{33}$)—CH= or —CH=CH—CO—CH=, where $R_{33}$ is as defined above; where:

(C-I) $R_{11}$ is $\alpha$-$R_{111}$:$\beta$-$R_{112}$, where one of $R_{111}$ and $R_{112}$ is taken together with $R_9$ to form a second bond between $C_9$ and $C_{11}$ and the other of $R_{111}$ and $R_{112}$ is —H;

(C-II) $R_9$ is —Cl and $R_{11}$ is =O or $\alpha$-H:$\beta$-$R_{114}$ where $R_{114}$ is —Cl or —OH;

(C-III) $R_9$ is —H or —F and $R_{11}$ is =O or $\alpha$-$R_{115}$:$\beta$-$R_{116}$, where one of $R_{115}$ and $R_{116}$ is —H, and the other of $R_{115}$ and $R_{116}$ is —H, —OH or $C_1$-$C_{12}$ alkoxy;

(C-IV) $R_9$ is —H or —F and $R_{11}$ is $\alpha$-O—CO—$R_{117}$: $\beta$-H, where $R_{117}$ is (A) $C_1$-$C_3$ alkyl,
(B) $C_1$-$C_{12}$ alkoxy,
(C) furanyl,
(D) —$NR_{122}R_{123}$, where one of $R_{122}$ and $R_{123}$ is —H, methyl or ethyl and the other is —H, $C_1$-$C_4$ alkyl or phenyl,
(E) —$X_3$—$X_1$, where $X_3$ is —O— or a valence bond, where $X_1$ is phenyl optionally substituted with 1 through 2 —Cl, —Br, $C_1$-$C_3$ alkoxy, —COOH, —$NH_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino and —NH—CHO or with 1 —F or —$CF_3$;

where:
(D-I) $R_{16}$ is $R_{161}$:$R_{162}$ and $R_{17}$ is $R_{171}$:$R_{172}$, where one of $R_{161}$ and $R_{162}$ is —H or —$CH_3$ and the other taken together with one of $R_{171}$ and $R_{172}$ forms a second bond between $C_{16}$ and $C_{17}$, and the other of $R_{171}$ and $R_{172}$ is —C(=Z)—$(CH_2)_n$—$NR_{21}R_{210}$, where Z is =O, =$CH_2$ or $R_{179}$:—H where $R_{179}$ is —H or —$CH_3$, where n is 0 through 6, where (A) $R_{21}$ is
(1) —$(CH_2)_m$—$NR_{211}$—$X_2$, where m is 2, 3 or 4, where $R_{211}$ is —H or $C_1$-$C_3$ alkyl, where $X_2$ is:
[A]
(a) pyridin-2-, 3- or 4-yl or the N-oxide thereof optionally substituted by 1 or 2 $R_{212}$, being the same or different, where $R_{212}$ is
(i) —F,
(ii) —Cl,
(iii) —Br,
(iv) $C_1$-$C_5$ alkyl,
(v) —$CH_2$—CH=$CH_2$,
(vi) —$X_1$, where $X_1$ is as defined above,
(vii) —$NR_{213}R_{213}$ where the $R_{213}$'s are the same or different and are —H, $C_1$-$C_3$ alkyl or —$CH_2$—CH=$CH_2$,
(viii$\alpha$) *$CH_2$—$(CH_2)_q$—$CH_2$—N*—where the atoms marked with an asterisk (*) are bonded to each other resulting in the formation of a ring, where q is 1 through 5,
(viii$\beta$) *$CH_2$—$CH_2$—$(CH_2)_c$—G—$(CH_2)_d$—$CH_2$—$CH_2$—N*— where the atoms marked with an asterisk (*) are bonded to each other resulting in the formation of a ring, where G is —O—, —S—, —SO—, —$SO_2$— or —$NHR_{214}$, where $R_{214}$ is —H, $C_1$-$C_3$ alkyl, or $X_1$ as defined above, where c and d are the same or different and are 0 through 2 with the proviso that the total number of ring carbon atoms is 4, 5 or 6, [a]
(ix) 3-pyrrolin-1-yl, [b]
(x) pyrrol-1-yl optionally substituted with $C_1$-$C_3$ alkyl, [c]
(xi) piperidin-1-yl optionally substituted with 1 or 2 $C_1$-$C_3$ alkyl, [d]
(xii) 1,2,3,6-tetrahydro-pyridin-1-yl, [e]
(xiii) 1-hexamethyleneimino containing a 3- or 4- double bond or 3- and 5-double bonds, [f]
(xiv) 1,4-dihydro-1-pyridinyl substituted in the 4 position by two $C_1$-$C_3$ alkyl being the same or different, [g]
(xv) —OH,
(xvi) $C_1$-$C_3$ alkoxy,
(xvii) —$NR_{217}$—$(CH_2)_e$—Q where Q is 2-pyridinyl where $R_{217}$ is —H or $C_1$-$C_3$ alkyl and e is 0 through 3 (1)
(xviii) pyridin-2-, 3- or 4-yl,
(b) 1,3,5-triazin-4-yl or the N-oxide thereof optionally substituted at the 2- and/or 6-position with $R_{212}$ as is defined above, (4)
(c) pyrimidin-4-yl or the N-oxide thereof optionally substituted at the 2- and/or 6-position with $R_{212}$ as is defined above, (5)
(d) pyrimidin-2-yl optionally substituted at the 4- and/or 6-position with 1 or 2 $R_{212}$ as is defined above, (6)
(e) pyrazin-2-yl optionally substituted with 1 or 2 $R_{212}$ as is defined above, (7)
(f) imidazol-2-yl optionally substituted in the 1 position with $C_1$-$C_3$ alkyl or —$X_1$, where $X_1$ is as defined above, and further optionally substituted with 1 or 2 $R_{212}$ as is defined above, (8)
(g) 1,3,4-triazol-2-yl optionally substituted in the 1 position with $C_1$-$C_3$ alkyl or —$X_1$, where $X_1$ is as defined above, and further optionally substituted with $R_{212}$ as is defined above, (9)
(h) imidazol-4- or 5-yl optionally substituted in the 1 position with $C_1$-$C_3$ alkyl or —$X_1$, where $X_1$ is as defined above, and further optionally substituted with 1 or 2 $R_{212}$ as is defined above, (10)
(i) benzo[b]thien-2-yl, (12a)
(j) indol-2-yl, (12b)
(k) benzo[b]thiazol-2-yl, (12c)
(l) benzimidazol-2-yl, (12d)
(m) 4-[2-[4-[2,6-bis(1-pyrrolidinyl)-4-pyrimidinyl]-1-piperazinyl]ethyl]piperazinyl, (13)
(n) 1,2,4-triazin-3-yl optionally substituted at the 5- and/or 6-position with $R_{212}$ as is defined above, (14)
(2) (1-piperazinyl)-($C_2$-$C_4$)alkyl optionally substituted in the 4-position with —$X_1$ or —$X_2$ as defined above, [B]
(3) —$X_2$, as defined above, [O]
(4) —$(CH_2)_m$—$X_4$ where m is as defined above and where $X_4$ is
(a) —O—$CH_2CH_2$—Y, where Y is $C_1$-$C_3$ alkylamino, di($C_1$-$C_3$) alkylamino where the alkyl groups are the same or different, $C_3$-$C_6$alkyleneimino, optionally substituted with 1 or 2 $C_1$-$C_3$ alkyl,
(b) —$NR_{220}CH_2CH_2$—Y, where $R_{220}$ is —H or $C_1$-$C_3$ alkyl and Y is as defined above,
(c) —$(CH_2)_g$—N($R_{220}$)—$X_2$, where g is 2, 3 or 4, and where $R_{220}$ and $X_2$ are as defined above, [H]
(5) —$(CH_2)_m$—$NR_{222}R_{223}$, where $R_{222}$ is —H or $C_1$-$C_3$ alkyl and $R_{223}$ is —$X_1$ or —$X_2$ as defined above, or $R_{222}$ and $R_{223}$ are taken together with the attached nitrogen atom to form a saturated mono-nitrogen $C_3$-$C_6$ heterocyclic ring and where m is as defined above, [I]

(6) —$(CHCH_3)_b$—$(CH_2)_f$—$R_{224}$, where b is 0 and f is 1 through 3 or b is one and f is 0 through 3, where $R_{224}$ is phenyl substituted with 1 through 3 —OH, $C_1$-$C_3$ alkoxy, —$NR_{225}R_{226}$ where $R_{225}$ and $R_{226}$ are the same or different and are —H, $C_1$-$C_3$ alkyl or are taken together with the attached nitrogen atom to form a $C_4$-$C_7$ cyclic amino ring, [J]

(7) —$(CH_2)_i$—$X_2$, where i is 1 through 4 and $X_2$ is as defined above, [K]

(8) (1-piperazinyl)acetyl substituted in the 4-position by $X_2$ where $X_2$ is as defined above, [L]

(9) (1-piperazinyl)carbonylmethyl substituted in the 4-position by -$X_2$ where $X_2$ is as defined above, and [M]

(B) $R_{210}$ is (1) —H, (2) $C_1$-$C_3$ alkyl, (3) $C_5$-$C_7$ cycloalkyl, (4) —$(CH_2)_m$—$NR_{211}$—$X_2$, where m, $R_{211}$ and $X_2$ are as defined above, [A]

(5) (1-piperazinyl)-($C_2$-$C_4$)alkyl optionally substituted in the 4-position with —$X_1$ or —$X_2$ as defined above, [B]

(6) —$(CH_2)_m$—$X_4$, where m and $X_4$ are as defined above, [H]

(7) —$(CH_2)_m$—$NR_{222}R_{223}$, where m, $R_{222}$ and $R_{223}$ are as defined above, [I]

(8) —$(CHCH_3)_b$—$(CH_2)_f$—$R_{224}$, where b, f and $R_{224}$ are as defined above, [J]

(C) $R_{21}$ and $R_{210}$ are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, [C-1]

(2) 2-(carboxy)-1-piperidinyl optionally as the $C_1$-$C_3$ alkyl ester or as a pharmaceutically acceptable salt, [C-2]

(3) 2-(carboxy)-1-hexamethyleneimino optionally as the $C_1$-$C_3$ alkyl ester or as a pharmaceutically acceptable salt, [C-3]

(4) 2-(carboxy)-1-heptamethylene-imino optionally as the $C_1$-$C_3$ alkyl ester or as a pharmaceutically acceptable salt, [C-4]

(5) 1-piperazinyl substituted in the 4-position with $R_{228}$—CO—$(CH_2)_j$— where $R_{228}$ is —$X_1$, —$NR_{229}X_1$ or 2-furanyl, where $R_{229}$ is —H or $C_1$-$C_3$ alkyl, where j is 0 through 3 and $X_1$ is as defined above, [D]

(6) 1-piperazinyl substituted in the 4-position with $X_2$—$(CH_2)_j$—, where $X_2$ and j are as defined above, [E]

(7) 1-piperazinyl substituted in the 4-position with $X_1$—$(CH_2)_j$—, where $X_1$ and j are as defined above, [F]

(8) 4-hydroxy-1-piperidinyl substituted in the 4-position with $X_1$ as defined above, [G]

(9) 1-piperazinyl substituted in the 4-position with $X_2$—$NR_{229}$—CO—$(CH_2)_i$—, where $X_2$, $R_{229}$ and i are as defined above; [N]

(D-II) $R_{16}$ is $\alpha$-$R_{163}$:$\beta$-$R_{164}$ where one of $R_{163}$ and $R_{164}$ is —H and the other is —H, —F, —$CH_3$ or —OH, and $R_{17}$ is —CH—$(CH_2)_p$—$NR_{21}R_{210}$, where p is 1 or 2, where $R_{21}$ and $R_{210}$ are as defined above;

(D-III) $R_{16}$ is $\alpha$-$R_{165}$:$\beta$-$R_{166}$ and $R_{17}$ is $\alpha$-$R_{175}$:$\beta$-$R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2$-$C_7$ alkanoyloxy or —O—CO—$X_1$, where $X_1$ is as defined above, and where $R_{176}$ is —C(=Z)—$(CH_2)_n$—$NR_{21}R_{210}$, where Z, n, $R_{21}$ and $R_{210}$ are as defined above;

(D-IV) the 16, 17-acetonide of a compound where $R_{165}$ is —OH, $R_{166}$ is —H, $R_{175}$ is —OH and $R_{176}$ is —C(=Z)—$(CH_2)_n$—$NR_{21}R_{210}$, where Z, n, —$R_{21}$ and $R_{210}$ are as defined above;

and the pharmaceutically acceptable salts, hydrates and solvates thereof;

with the following overall provisos that:

(I) one of $R_{161}$ or $R_{162}$ is taken together with one of $R_{171}$ or $R_{172}$ to form a second bond between $C_{16}$ and $C_{17}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$: $\beta$-$R_{1010}$, (II) $R_{17}$ is —CH—$(CH_2)_p$—$NR_{21}R_{210}$, only when $R_{10}$ is $\alpha$-$R_{101}$:$\beta$-$R_{102}$, $\alpha$-$R_{103}$:$\beta$-$R_{108}$ or $\alpha$-$R_{109}$:$\beta$-$R_{1010}$, (III) $R_5$ and $R_{10}$ taken together are =CH—CH= C($OR_3$)—CH=, only when $R_{17}$ is $\alpha$-$R_{175}$:$\beta$-$R_{176}$ or the 16,17-acetonide of a compound where $R_{16}$ is $\alpha$-OH: $\beta$-H and $R_{17}$ is $\alpha$-OH: $\beta$C(=Z)—$(CH_2)_n$—$NR_{21}R_{210}$, and (IV) $R_5$ is $\alpha$-$R_{57}$:$\beta$-$R_{58}$, only when $R_{17}$ is $\alpha$-$R_{175}$:$\beta$-$R_{176}$ or $\alpha$-OH: $\beta$-C—(=Z)—$(CH_2)_n$—$NR_{21}R_{210}$, or the 16,17-acetonide thereof; and (b) an orally acceptable carrier therefor comprising lightly cross-linked carboxy-containing polymer and water.

15. The composition according to claim 14, comprising from about 0.1% to about 2.0% by weight of said therapeutic agent.

16. The composition according to claim 14, wherein said polymer is polycarbophil.

17. The composition according to claim 14, further comprising one or more additives selected from the group consisting of sodium edetate, methyl paraben, propyl paraben, flavoring agents and colorants.

18. The composition according to claim 14 wherein said lightly cross-linked carboxy-containing polymer is a polyalkenyl polyether, lightly crosslinked carboxy-containing polymer.

19. A pharmaceutical composition for topical administration comprising:

(a) from about 0.01 to about 10% by weight of an amino-substituted steroid therapeutic agent selected from the group consisting of the $C_{20}$ through $C_{26}$ aminosteroids of the formula XI

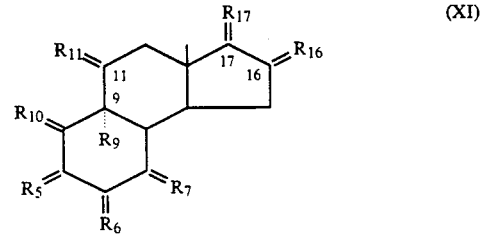

where (A-I) $R_6$ is $\alpha$-$R_{61}$:$\beta$-$R_{62}$, $R_{10}$ is $\alpha$-$R_{101}$:$\beta$-$R_{102}$ and $R_7$ is $\alpha$-H: $\beta$-H, where one of $R_{61}$ and $R_{62}$ is —H, and the other is —H, —F, or $C_1$-$C_3$ alkyl, $R_{102}$ is $CH_3$, $R_{101}$ and $R_5$ taken together are —$(CH_2)_2$—C(—$R_{33}$)=CH— or —CH—CH—CO—CH=, where $R_{33}$ is =O or $\alpha$-H: $\beta$-$OR_{34}$: $\beta$-H, where $R_{34}$ is —H, —P(=O)(OH)$_2$, —CO—$CH_3$, —CO—$C_2H_5$, —CO—$C_6H_5$, —CO—O—$CH_3$ or —CO—O—$C_2H_5$;

(A-II) $R_5$ is $\alpha$-$R_{53}$:$\beta$-$R_{54}$, $R_6$ is $\alpha$-$R_{63}$:$\beta$-$R_{64}$, $R_{10}$ is $\alpha$-$R_{103}$:$\beta$-$R_{104}$ $R_7$ is $\alpha$-H: $\beta$-H, where one of $R_{63}$ and $R_{64}$ is —H, and the other taken together with one of $R_{53}$ and $R_{54}$ forms a second bond between $C_5$ and $C_6$, $R_{104}$ is —$CH_3$, $R_{103}$ and the other of $R_{53}$ and $R_{54}$ taken together are —$(CH_2)_2$—C(H)(OH)—$CH_2$— or —$(CH_2)_2$—C[H][OP(=O)—(OH)$_2$]—$CH_2$—;

(A-III) $R_{10}$ and $R_5$ taken together are =CH—CH=C($OR_3$)—CH= where $R_3$ is —H, —P(=O)(OH)$_2$, $C_1$-$C_3$ alkyl, —CO—H, $C_2$-$C_4$ alkanoyl or benzyl, $R_6$ is $\alpha$-$R_{65}$:$\beta$-$R_{66}$ where one of $R_{65}$ and $R_{66}$ is —H, and the other is —H, —F, or $C_1$-$C_3$ alkyl and $R_7$ is $\alpha$-H: $\beta$-H;

(A-IV) $R_5$ is $\alpha$-$R_{57}$:$\beta$-$R_{58}$, $R_6$ is $\alpha$-H: $\beta$-H and $R_{10}$ is $\alpha$-$R_{107}$:$\beta$-$R_{108}$, where one of $R_{57}$ and $R_{58}$ is —H, $R_{107}$ and the other of $R_{57}$ and $R_{58}$ taken together are —$(CH_2)_2$—C(=$R_{33}$)—$CH_2$, where $R_{33}$ is as defined above, $R_{108}$ is —$CH_3$, where one of $R_{67}$ and $R_{68}$ is —H and the other is —H, —F, or $C_1$-$C_3$ alkyl;

(A-V) $R_6$ is $R_{69}$:$R_{610}$, $R_7$ is $R_{79}$: $R_{710}$, $R_{10}$ is $\alpha$-$R_{109}$:$R_{1010}$, where one of $R_{69}$ and $R_{610}$ is —H and the other taken together with one of $R_{79}$ and $R_{710}$ forms a second bond between $C_6$ and $C_7$, and the other of $R_{79}$ and $R_{710}$ is —H, $R_{1010}$ is —$CH_3$, $R_{109}$ and $R_5$ taken together are —$(CH_2)_2$—C(=$R_{33}$)—CH= or —CH=CH—CO—CH=, where $R_{33}$ is as defined above; where;

(C-I) $R_{11}$ is $\alpha$-$R_{111}$:$\beta$-$R_{112}$, where one of $R_{111}$ and $R_{112}$ is taken together with $R_9$ to form a second bond between $C_9$ and $C_{11}$ and the other of $R_{111}$ and $R_{112}$ is —H;

(C-II) $R_9$ is —Cl and $R_{11}$ is =O or $\alpha$-H:$\beta$-$R_{114}$ where $R_{114}$ is —Cl or —OH;

(C-III) $R_9$ is —H or —F and $R_{11}$ is =O or $\alpha$-$R_{115}$:$\beta$-$R_{116}$, where one of $R_{115}$ and $R_{116}$ is —H, and the other of $R_{115}$ and $R_{116}$ is —H, —OH or $C_1$-$C_{12}$ alkoxy;

(C-IV) $R_9$ is —H or —F and $R_{11}$ is $\alpha$-O—CO—$R_{117}$: $\beta$-H, where $R_{117}$ is (A) $C_1$-$C_3$ alkyl,
(B) $C_1$-$C_{12}$ alkoxy,
(C) furanyl,
(D) —$NR_{122}R_{123}$, where one of $R_{122}$ and $R_{123}$ is —H, methyl or ethyl and the other is —H, $C_1$-$C_4$ alkyl or phenyl,
(E) —$X_3$—$X_1$, where $X_3$ is —O— or a valence bond, where $X_1$ is phenyl optionally substituted with 1 through 2 —Cl, —Br, $C_1$-$C_3$ alkoxy, —COOH, —$NH_2$, $C_1$-$C_3$ alkylamino, di($C_1$-$C_3$)alkylamino, where the alkyl groups are the same or different, 1-pyrrolidinyl-, 1-piperidinyl-, 1-hexamethylenimino-, 1-heptamethylenimino-, $C_2$-$C_4$ acylamino and —NH—CHO or with 1 —F or —$CF_3$;

where:

(D-I) $R_{16}$ is $R_{161}$:$R_{162}$ and $R_{17}$ is $R_{171}$:$R_{172}$, where one of $R_{161}$ and $R_{162}$ is —H or —$CH_3$ and the other taken together with one of $R_{171}$ and $R_{172}$ forms a second bond between $C_{16}$ and $C_{17}$ and the other of $R_{171}$ and $R_{172}$ is —C(=Z)—$(CH_2)_n$—$NR_{21}R_{210}$, where Z is =O, =$CH_2$ or $R_{179}$: —H where $R_{179}$ is —H or —$CH_3$, where n is 0 through 6, where (A) $R_{21}$ is (1) —$(CH_2)_m$—$NR_{211}$—$X_2$, where m is 2, 3 or 4, where $R_{211}$ is —H or $C_1$-$C_3$ alkyl, where $X_2$ is:
[A]
(a) pyridin-2-, 3- or 4-yl or the N-oxide thereof optionally substituted by 1 or 2 $R_{212}$, being the same or different, where $R_{212}$ is
  (i) —F,
  (ii) —Cl,
  (iii) —Br,
  (iv) $C_1$-$C_5$ alkyl,
  (v) —$CH_2$—CH=$CH_2$,
  (vi) —$X_1$, where $X_1$ is as defined above,
  (vii) —$NR_{213}R_{213}$ where the $R_{213}$'s are the same or different and are —H, $C_1$-$C_3$ alkyl or —$CH_2$—CH=$CH_2$,
  (viii$\alpha$) *$CH_2$—$(CH_2)_q$—$CH_2$—N*— where the atoms marked with an asterisk (*) are bonded to each other resulting in the formation of a ring, where q is 1 through 5,
  (viii$\beta$) *$CH_2$—$CH_2$—$(CH_2)_c$—G—$(CH_2)_d$—$CH_2$—$CH_2$—N*— where the atoms marked with an asterisk (*) are bonded to each other resulting in the formation of a ring, where G is —O—, —S—, —SO—, —$SO_2$— or —$NHR_{214}$, where $R_{214}$ is —H, $C_1$-$C_3$ alkyl, or $X_1$ as defined above, where c and d are the same or different and are 0 through 2 with the proviso that the total number of ring carbon atoms is 4, 5 or 6, [a]
  (ix) 3-pyrrolin-1-yl, [b]
  (x) pyrrol-1-yl optionally substituted with $C_1$-$C_3$ alkyl, [c]
  (xi) piperidin-1-yl optionally substituted with 1 or 2 $C_1$-$C_3$ alkyl, [d]
  (xii) 1,2,3,6-tetrahydropyridin-1-yl, [e]
  (xiii) 1-hexamethyleneimino containing a 3- or 4-double bond or 3- and 5-double bonds, [f]
  (xiv) 1,4-dihydro-1-pyridinyl substituted in the 4 position by two $C_1$-$C_3$ alkyl being the same or different, [g]
  (xv) —OH,
  (xvi) $C_1$-$C_3$ alkoxy,
  (xvii) —$NR_{217}$—$(CH_2)_e$—Q where Q is 2-pyridinyl where $R_{217}$ is —H or $C_1$-$C_3$ alkyl and e is 0 through 3 (1)
  (xviii) pyridin-2-, 3- or 4-yl,
(b) 1,3,5-triazin-4-yl or the N-oxide thereof optionally substituted at the 2- and/or 6-position with $R_{212}$ as is defined above, (4)
(c) pyrimidin-4-yl or the N-oxide thereof optionally substituted at the 2- and/or 6-position with $R_{212}$ as is defined above, (5)
(d) pyrimidin-2-yl optionally substituted at the 4- and/or 6-position with 1 or 2 $R_{212}$ as is defined above, (6)
(e) pyrazin-2-yl optionally substituted with 1 or 2 $R_{212}$ as is defined above, (7)
(f) imidazol-2-yl optionally substituted in the 1 position with $C_1$-$C_3$ alkyl or —$X_1$, where $X_1$ is as defined above, and further optionally substituted with 1 or 2 $R_{212}$ as defined above, (8)

(g) 1,3,4-triazol-2-yl optionally substituted in the 1 position with $C_1$-$C_3$ alkyl or —$X_1$, where $X_1$ is as defined above, and further optionally substituted with $R_{212}$ as defined above, (9)

(h) imidazol-4- or 5-yl optionally substituted in the 1 position with $C_1$-$C_3$ alkyl or —$X_1$, where $X_1$ is as defined above, and further optionally substituted with 1 or 2 $R_{212}$ as defined above, (10)

(i) benzo[b]thien-2-yl, (12a)

(j) indol-2-yl, (12b)

(k) benzo[b]thiazol-2-yl, (12c)

(l) benzimidazol-2-yl, (12d)

(m) 4-[2-[4-[2,6-bis(1-pyrrolidinyl)-4-pyrimidinyl]-1-piperazinyl]ethyl]piperazinyl, (13)

(n) 1,2,4-triazin-3-yl optionally substituted at the 5- and/or 6-position with $R_{212}$ as is defined above, (14)

(2) (1-piperazinyl)-($C_2$-$C_4$)alkyl optionally substituted in the 4-position with —$X_1$ or —$X_2$ as defined above, [B]

(3) —$X_2$, as defined above, [O]

(4) —$(CH_2)_m$—$X_4$ where m is as defined above and where $X_4$ is (a) —O—$CH_2CH_2$—Y, where Y is $C_1$-$C_3$ alkylamino, di($C_1$-$C_3$)alkylamino where the alkyl groups are the same or different, $C_3$-$C_6$ alkyleneimino, optionally substituted with 1 or 2 $C_1$-$C_3$ alkyl, (b) —$NR_{220}CH_2CH_2$—Y, where $R_{220}$ is —H or $C_1$-$C_3$ alkyl and Y is as defined above, (c) —$(CH_2)_g$—$N(R_{220})$—$X_2$, where g is 2, 3 or 4, and where $R_{220}$ and $X_2$ are as defined above, [H]

(5) —$(CH_z)_m$—$NR_{222}R_{223}$, where $R_{222}$ is —H or $C_1$-$C_3$ alkyl and $R_{223}$ is —$X_1$ or —$X_2$ as defined above, or $R_{222}$ and $R_{223}$ are taken together with the attached nitrogen atom to form a saturated mono-nitrogen $C_3$-$C_6$ heterocyclic ring and where m is as defined above, [I]

(6) —$(CHCH_3)_b$—$(CH_2)_f$—$R_{224}$, where b is 0 and f is 1 through 3 or b is one and f is 0 through 3, where $R_{224}$ is phenyl substituted with 1 through 3 —OH, $C_1$-$C_3$ alkoxy, —$NR_{225}R_{226}$ where $R_{225}$ and $R_{226}$ are the same or different and are —H, $C_1$-$C_3$ alkyl or are taken together with the attached nitrogen atom to form a $C_4$-$C_7$ cyclic amino ring, [J]

(7) —$(CH_2)_i$—$X_2$, where i is 1 through 4 and $X_2$ is as defined above, [K]

(8) (1-piperazinyl)acetyl substituted in the 4-position by $X_2$ where $X_2$ is as defined above, [L]

(9) (1-piperazinyl)carbonylmethyl substituted in the 4-position by —$X_2$ where $X_2$ is as defined above, and [M]45-152

(B) $R_{210}$ is (1) —H, (2) $C_1$-$C_3$ alkyl, (3) $C_5$-$C_7$ cycloalkyl, (4) —$(CH_2)_m$—$NR_{211}$—$X_2$, where m, $R_{211}$ and $X_2$ are as defined above, [A]

(5) (1-piperazinyl)-($C_2$-$C_4$)alkyl optionally substituted in the 4-position with —$X_1$ or —$X_2$ as defined above, [B]

(6) —$(CH_2)_m$—$X_4$, where m and $X_4$ are as defined above, [H]

(7) —$(CH_2)_m$—$NR_{222}R_{223}$, where m, $R_{222}$ and $R_{223}$ are as defined above, [I]

(8) —$(CHCH_3)_b$—$(CH_2)_f$—$R_{224}$, where b, f and $R_{224}$ are as defined above, [J]

(C) $R_{21}$ and $R_{210}$ m are taken together with the attached nitrogen atom to form a heterocyclic ring selected from the group consisting of (1) 2-(carboxy)-1-pyrrolidinyl optionally as the $C_1$-$C_3$ alkyl ester or as a pharmaceutically acceptable salt, [C-1]

(2) 2-(carboxy)-1-piperidinyl optionally as the $C_1$-$C_3$ alkyl ester or as a pharmaceutically acceptable salt, [C-2]

(3) 2-(carboxy)-1-hexamethyleneimino optionally as the $C_1$-$C_3$ alkyl ester or as a pharmaceutically acceptable salt, [C-3]

(4) 2-(carboxy)-1-heptamethylene-imino optionally as the $C_1$-$C_3$ alkyl ester or as a pharmaceutically acceptable salt, [C-4]

(5) 1-piperazinyl substituted in the 4-position with $R_{228}$—CO—$(CH_2)_j$— where $R_{228}$ is —$X_1$, —$NR_{229}X_1$ or 2-furanyl, where $R_{229}$ is —H or $C_1$-$C_3$ alkyl, where j is 0 through 3 and $X_1$ is as defined above, [D]

(6) 1-piperazinyl substituted in the 4-position with $X_2$—$(CH_2)_j$—, where $X_2$ and j are as defined above, [E]

(7) 1-piperazinyl substituted in the 4-position with $X_1$—$(CH_2)_j$—, where $X_1$ and j are as defined above, [F]

(8) 4-hydroxy-1-piperidinyl substituted in the 4-position with $X_1$ as defined above, [G]

(9) 1-piperazinyl substituted in the 4-position with $X_2$—$N_{229}$—CO—$(CH_2)_i$—, where $X_2$, $R_{229}$ and i are as defined above; [N]

(D-II) $R_{16}$ is $\alpha$-$R_{163}$:$\beta$-$R_{164}$ where one of $R_{163}$ and $R_{164}$ is —H and the other is —H, —F, —$CH_3$ or —OH, and $R_{17}$ is —CH—$(CH_2)_p$—$NR_{21}R_{210}$, where p is 1 or 2, where $R_{21}$ and $R_{210}$ are as defined above;

(D-III) $R_{16}$ is $\alpha$-$R_{165}$:$\beta$-$R_{166}$ and $R_{17}$ is $\alpha$-$R_{175}$:$\beta$-$R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2$-$C_7$ alkanoyloxy or —O—CO—$X_1$, where $X_1$ is as defined above, and where $R_{176}$ is —C(=Z)—$(CH_2)_n$—$NR_{21}R_{210}$, Z, n, $R_{21}$ and $R_{210}$ are as defined above;

(D-IV) the 16,17-acetonide of a compound where $R_{165}$ is —OH, $R_{166}$ is —H, $R_{175}$ is —OH and $R_{176}$ is —C(=Z)—$(CH_2)_n$—$NR_{21}R_{210}$, where Z, n, —$R_{21}$ and $R_{210}$ are as defined above;

and the pharmaceutically acceptable salts, hydrates and solvates thereof;

with the following overall provisos that:

(I) one of $R_{161}$ or $R_{162}$ is taken together with one of $R_{171}$ or $R_{172}$ to form a second bond between $C_{16}$ and $C_{17}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (II) $R_{17}$ is —CH—$(CH_2)_p$—$NR_{21}R_{210}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (III) $R_5$ and $R_{10}$ taken together are =CH—CH=C(OR_3)—CH=, only when $R_{17}$ is $\alpha$-$R_{175}$:$\beta$-$R_{176}$ or the 16,17-acetonide of a compound where $R_{16}$ is $\alpha$-OH: $\beta$-H and $R_{17}$ is $\alpha$-OH: $\beta$-C(=Z)—$(CH_2)_n$—$NR_{21}R_{210}$, and (IV) $R_5$ is $\alpha$-$R_{57}$:$\beta$-$R_{58}$, only when $R_{17}$ is $\alpha$-$R_{175}$:$\beta$-$R_{176}$ or $\alpha$-OH: $\beta$-C—(=Z)—(CH$_2$)$_n$—NR$_{211}$R$_{210}$, or the 16,17-acetonide thereof; and (b) a topically acceptable carrier therefor comprising lightly cross-linked carboxy-containing polymer and water.

20. The composition according to claim 19, comprising from about 0.1 to about 5% by weight of said therapeutic agent.

21. The composition according to claim 19, wherein said polymer is a suspension-polymerized acrylic acid and divinyl glycol.

22. The composition according to claim 19 wherein the polymer is a polyalkenyl polyether, lightly cross-linked carboxy-containing polymer.

23. The composition according to claim 19, wherein the therapeutic agent is selected from the group consisting of 21-[4-(2,6-dipyrrolidinyl-4-pyrimidinyl)-1-piperazinyl]-16$\alpha$-methylpregna-1,4,9(11)-triene-3,20-dione, or a pharmaceutically acceptable salt, hydrate or solvate thereof; 21-[4-[5,6-bis(diethylamino)-2-pyridinyl]-1-piperazinyl]-16$\alpha$-methylpregna-1,4,9(11)-triene-3,20-dione, or a pharmaceutically acceptable salt, hydrate or solvate thereof; and 21-[4-(3-ethylamino-2-pyridinyl)-1-piperazinyl]-16$\alpha$-methylpregna-1,4,9(11)-triene-3,20-dione, or a pharmaceutically acceptable salt, hydrate or solvate thereof.

24. The composition according to claim 19 wherein the therapeutic agent is selected from the group consisting of the methanesulfonate salt of the methanesulfonate salt of 21-[4-(2,6-dipyrrolidinyl-4-pyrimidinyl)-1-piperazinyl]-16$\alpha$-methylpregna- 1,4,9(11)-triene-3,20-dione; the hydrochloride salt of 21-[4-[5,6-bis(diethylamino)-2-pyridinyl]-1-piperazinyl]-16$\alpha$-methylpregna-1,4,9(11)-triene-3,20-dione; and the hydrochloride or maleic acid salt of 21-[4-(3-ethylamino-2-pyridinyl)-1-piperazinyl]-16$\alpha$-methylpregna-1,4,9(11)-triene-3,20-dione.

25. A pharmaceutical composition comprising an amino-substituted steroid therapeutic agent selected from the group consisting of the $C_{20}$ through $C_{26}$ aminosteroids of the formula XI

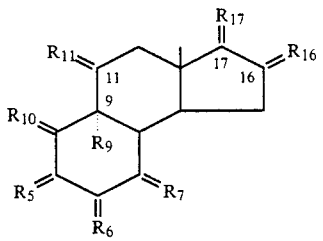
(XI)

where:
(A-I) $R_6$ is $\alpha$-$R_{61}$:$\beta$-$R_{62}$, $R_{10}$ is $\alpha$-$R_{101}$:$\beta$-$R_{102}$ and $R_7$ is $\alpha$-H: $\beta$-H, where one of $R_{61}$ and $R_{62}$ is —H, and the other is —H, —F, or $C_1$-$C_3$ alkyl, $R_{102}$ is —CH$_3$, $R_{101}$ and $R_5$ taken together are —(CH$_2$)$_2$—C(—R$_{33}$)—CH= or —CH—CH—CO—CH=, where $R_{33}$ is =O or $\alpha$-H: $\beta$-OR$_{34}$ or $\alpha$-OR$_{34}$: $\beta$-H, where $R_{34}$ is —H, —P(=O)(OH)$_2$, —CO—CH$_3$, —CO—C$_2$H$_5$, —CO—C$_6$H$_5$, —CO—O—CH$_3$ or —CO—O—C$_2$H$_5$;

(A-II) $R_5$ is $\alpha$-$R_{53}$:$\beta$-$R_{54}$, $R_6$ is $\alpha$-$R_{63}$:$\beta$-$R_{64}$, $R_{10}$ is $\alpha$-$R_{103}$: $\beta$-$R_{104}$ and $R_7$ is $\alpha$-H: $\beta$-H, where one of $R_{63}$ and $R_{64}$ is —H, and the other taken together with one of $R_{53}$ and $R_{54}$ forms a second bond between $C_5$ and $C_6$, $R_{104}$ is —CH$_3$, $R_{103}$ and the other of $R_{53}$ and $R_{54}$ taken together are —(CH$_2$)$_2$—C(H)(OH)—CH$_2$— or —(CH$_2$)$_2$—C[H][OP(=O)—(OH)$_2$]—CH$_2$—

(A-III) $R_{10}$ and $R_5$ taken together are =CH—CH=C(OR$_3$)—CH= where $R_3$ is —H, —P(=O)(OH)$_2$, $C_1$-$C_3$ alkyl, —CO—H, $C_2$-$C_4$ alkanoyl or benzyl, $R_6$ is $\alpha$-$R_{65}$:$\beta$-$R_{66}$ where one of $R_{65}$ and $R_{66}$ is —H, and the other is —H, —F, or $C_1$-$C_3$ alkyl and $R_7$ is $\alpha$-H: $\beta$-H;

(A-IV) $R_5$ is $\alpha$-$R_{57}$:$\beta$-$R_{58}$, $R_6$ is $\alpha$-$R_{67}$:$\beta$-$R_{68}$, $R_7$ is $\alpha$-H: $\beta$-H and $R_{10}$ is $\alpha$-$R_{107}$:$\beta$-$R_{108}$, where one of $R_{57}$ and $R_{58}$ is —H, $R_{107}$ and the other of $R_{57}$ and $R_{58}$ taken together are —(CH$_2$)$_2$—C(=R$_{33}$)—CH$_2$, where $R_{33}$ is as defined above, $R_{108}$ is —CH$_3$, where one of $R_{67}$ and $R_{68}$ s is —H and the other is —H, —F, or $C_1$-$C_3$ alkyl;

(A-V) $R_6$ is $R_{69}$:$R_{610}$, $R_7$ is $R_{79}$:$R_{710}$, $R_{10}$ is $\alpha$-$R_{109}$:$R_{1010}$, where one of $R_{69}$ and $R_{610}$ is —H and the other taken together with one of $R_{79}$ and $R_{710}$ forms a second bond between $C_6$ and $C_7$, and the other of $R_{79}$ and $R_{710}$ is —H, $R_{1010}$ is —CH$_3$, $R_{109}$ and $R_5$ taken together are —(CH$_2$)$_2$—C(=R$_{33}$)—CH= or —CH=CH—CO—CH=, where $R_{33}$ is as defined above; where:

(C-I) $R_{11}$ is $\alpha$-$R_{111}$:$\beta$-$R_{112}$, where one of $R_{111}$ and $R_{112}$ is taken together with $R_9$ to form a second bond between $C_9$ and $C_{11}$ and the other of $R_{111}$ and $R_{112}$ is —H;

(C-II) $R_9$ is —Cl and $R_{11}$ is =O or $\alpha$-H:$\beta$-$R_{114}$ where $R_{114}$ is —Cl or —OH;

(C-III) $R_9$ is —H or —F and $R_{11}$ is =O or $\alpha$-$R_{115}$:$\beta$-$R_{165}$, where one of $R_{115}$ and $R_{116}$ is —H, and the other of $R_{115}$ and $R_{116}$ is —H, —OH or $C_1$-$C_{12}$ alkoxy;

(C-IV) $R_9$ is —H or —F and $R_{11}$ is $\alpha$-O—CO—$R_{117}$: $\beta$-H, where $R_{117}$ is (A) $C_1$-$C_3$ alkyl, (B) $C_1$-$C_{12}$ alkoxy, (C) furanyl, (D) —NR$_{122}$R$_{123}$, where one of $R_{122}$ and $R_{123}$ is —H, methyl or ethyl and the other is —H, $C_1$-$C_4$ alkyl or phenyl, (E) —X$_3$—X$_1$, where X$_3$ is —O— or a valence bond, where X$_1$ is phenyl optionally substituted with 1 through 2 —Cl, —Br, $C_1$-$C_3$ alkoxy, —COOH, —NH$_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-heptamethylenimino-, $C_2$-$C_4$ acylamino and —NH—CHO or with 1 —F or —CF$_3$;

where:
(D-I) $R_{16}$ is $R_{161}$:$R_{162}$ and $R_{17}$ is $R_{171}$:$R_{172}$, where one of $R_{161}$ and $R_{162}$ is —H or —CH$_3$ and the other taken together with one of $R_{171}$ and $R_{172}$ forms a second bond between $C_{16}$ and $C_{17}$, and the other of $R_{171}$ and $R_{172}$ is —C(=Z)—(CH$_2$)$_n$—NR$_{21}$R$_{210}$, where Z is =O, =CH$_2$ or $R_{179}$: —H where $R_{179}$ is —H or —CH$_3$, where n is 0 through 6, where (A) $R_{21}$ is
(1) —(CH$_2$)—NR$_{211}$-X$_2$, where m is 2, 3 or 4, where $R_{211}$ is —H or $C_1$-$C_3$ alkyl, where X$_2$ is:
[A]
(a) pyridin-2-, 3- or 4-yl or the N-oxide thereof optionally substituted by 1 or 2 $R_{212}$, being the same or different, where $R_{212}$ is
(i) —F,
(ii) —Cl, (iii) —Br,
(iv) $C_1$-$C_5$ alkyl,
(v) —$CH_2$—CH=$CH_2$,
(vi) —$X_1$, where $X_1$ is as defined above,
(vii) —$NR_{213}R_{213}$ where the $R_{213}$'s are the same or different and are —H, $C_1$-$C_3$ alkyl or —$CH_2$—CH=$CH_2$,
(viiiα) *$CH_2$—($CH_2$)$_q$—$CH_2$—N*— where the atoms marked with an asterisk (*) are bonded to each other resulting in the formation of a ring, where q is 1 through 5,
(viiiβ) *$CH_2$—$CH_2$—($CH_2$)$_c$—G—($CH_2$)$_d$—$CH_2$—$CH_2$—N*— where the atoms marked with an asterisk (*) are bonded to each other resulting in the formation of a ring, where G is —O—, —S—, —SO—, —$SO_2$— or —$NHR_{214}$, where $R_{214}$ is —H, $C_1$-$C_3$ alkyl, or $X_1$ as defined above, where c and d are the same or different and are 0 through 2 with the proviso that the total number of ring carbon atoms is 4, 5 or 6, [a]
(ix) 3-pyrrolin-1-yl, [b]
(x) pyrrol-1-yl optionally substituted with $C_1$-$C_3$ alkyl, [c]
(xi) piperidin-1-yl optionally substituted with 1 or 2 $C_1$-$C_3$ alkyl, [d]
(xii) 1,2,3,6-tetrahydro-pyridin-1-yl, [e]
(xiii) 1-hexamethyleneimino containing a 3- or 4-double bond or 3- and 5-double bonds, [f]
(xiv) 1,4-dihydro-1-pyridinyl substituted in the 4 position by two $C_1$-$C_3$ alkyl being the same or different, [g]
(xv) —OH,
(xvi) $C_1$-$C_3$ alkoxy,
(xvii) —$NR_{217}$—($CH_2$)$_e$—Q where Q is 2-pyridinyl where $R_{217}$ is —H or $C_1$-$C_3$ alkyl and e is 0 through 3 (1)
(xviii) pyridin-2-, 3- or 4-yl,
(b) 1,3,5-triazin-4-yl or the N-oxide thereof optionally substituted at the 2- and/or 6-position with $R_{212}$ as is defined above, (4)
(c) pyrimidin-4-yl or the N-oxide thereof optionally substituted at the 2- and/or 6-position with $R_{212}$ as is defined above, (5)
(d) pyrimidin-2-yl optionally substituted at the 4- and/or 6-position with 1 or 2 $R_{212}$ as is defined above, (6)
(e) pyrazin-2-yl optionally substituted with 1 or 2 $R_{212}$ as is defined above, (7)
(f) imidazol-2-yl optionally substituted in the 1 position with $C_1$-$C_3$ alkyl or —$X_1$, where $X_1$ is as defined above, and further optionally substituted with 1 or 2 $R_{212}$ as defined above, (8)
(g) 1,3,4-triazol-2-yl optionally substituted in the 1 position with $C_1$-$C_3$ alkyl or —$X_1$, where $X_1$ is as defined above, and further optionally substituted with $R_{212}$ as defined above, (9)
(h) imidazol-4- or 5-yl optionally substituted in the 1 position with $C_1$-$C_3$ alkyl or —$X_1$, where $X_1$ is as defined above, and further optionally substituted with 1 or 2 $R_{212}$ as defined above, (10)
(i) benzo[b]thien-2-yl, (12a)
(j) indol-2-yl, (12b)
(k) benzo[b]thiazol-2-yl, (12c)
(l) benzimidazol-2-yl, (12d)
(m) 4-[2-[4-[2,6-bis(1-pyrrolidinyl)-4-pyrimidinyl]-1-piperazinyl]ethyl]piperazinyl, (13)
(n) 1,2,4-triazin-3-yl optionally substituted at the 5- and/or 6-position with $R_{212}$ as is defined above, (14)
(2) (1-piperazinyl)-($C_2$-$C_4$)alkyl optionally substituted in the 4-position with —$X_1$ or —$X_2$ as defined above, [B]
(3) —$X_2$, as defined above, [O]
(4) —($CH_2$)$_m$—$X_4$ where m is as defined above and where $X_4$ is
  (a) —O—$CH_2CH_2$—Y, where Y is $C_1$-$C_3$ alkylamino, di($C_1$-$C_3$)alkylamino where the alkyl groups are the same or different, $C_3$-$C_6$ alkyleneimino, optionally substituted with 1 or 2 $C_1$-$C_3$ alkyl,
  (b) —$NR_{220}CH_2CH_2$—Y, where $R_{220}$ is —H or $C_1$-$C_3$ alkyl and Y is as defined above,
  (c) —($CH_2$)$_g$—N($R_{220}$)—$X_2$, where g is 2, 3 or 4, and where $R_{220}$ and $X_2$ are as defined above, [H]
(5) —($CH_2$)$_m$—$NR_{222}R_{223}$, where $R_{222}$ is —H or $C_1$-$C_3$ alkyl and $R_{223}$ is —$X_1$ or —$X_2$ as defined above, or $R_{222}$ and $R_{223}$ are taken together with the attached nitrogen atom to form a saturated mono-nitrogen $C_3$-$C_6$ heterocyclic ring and where m is as defined above, [I]
(6) —(CHCH$_3$)$_b$—($CH_2$)$_f$—$R_{224}$, where b is 0 and f is 1 through 3 or b is one and f is 0 through 3, where $R_{224}$ is phenyl substituted with 1 through 3 —OH, $C_1$-$C_3$ alkoxy, —$NR_{225}R_{226}$ where $R_{225}$ and $R_{226}$ are the same or different and are —H, $C_1$-$C_3$ alkyl or are taken together with the attached nitrogen atom to form a $C_4$-$C_7$ cyclic amino ring, [J]
(7) —($CH_2$)$_i$—$X_2$, where i is 1 through 4 and $X_2$ is as defined above, [K]
(8) (1-piperazinyl)acetyl substituted in the 4-position by $X_2$ where $X_2$ is as defined above, [L]
(9) (1-piperazinyl)carbonylmethyl substituted in the 4-position by —$X_2$ where $X_2$ is as defined above, and [M]
(B) $R_{210}$ is
  (1) —H,
  (2) $C_1$-$C_3$ alkyl,
  (3) $C_5$-$C_7$ cycloalkyl,
  (4) —($CH_2$)$_m$—$NR_{211}$—$X_2$, where m, $R_{211}$ and $X_2$ are as defined above, [A]
  (5) (1-piperazinyl)—($C_2$-$C_4$)alkyl optionally substituted in the 4-position with —$X_1$ or —$X_2$ as defined above, [B]
  (6) —($CH_2$)$_m$—$X_4$, where m and $X_4$ are as defined above, [H]
  (7) —($CH_2$)$_m$—$NR_{222}R_{223}$, where m, $R_{222}$ and $R_{223}$ are as defined above, [I]
  (8) —(CHCH$_3$)$_b$—($CH_2$)$_f$—$R_{224}$, where b, f and $R_{224}$ are as defined above, [J]
(C) $R_{21}$ and $R_{210}$ are taken together with the attached nitrogen atom to form a heterocyclic ring selected from the group consisting of
  (1) 2-(carboxy)-1-pyrrolidinyl optionally as the $C_1$-$C_3$ alkyl ester or as a pharmaceutically acceptable salt, [C-1]
  (2) 2-(carboxy)-1-piperidinyl optionally as the $C_1$-$C_3$ alkyl ester or as a pharmaceutically acceptable salt, [C-2]

(3) 2-(carboxy)- 1-hexamethyleneimino optionally as the $C_1$-$C_3$ alkyl ester or as a pharmaceutically acceptable salt, [C-3]

(4) 2-(carboxy)- 1-heptamethylene-imino optionally as the $C_1$-$C_3$ alkyl ester or as a pharmaceutically acceptable salt, [C-4]

(5) 1-piperazinyl substituted in the 4-position with $R_{228}$—CO—$(CH_2)_j$— where $R_{228}$ is —$X_1$, —$NR_{229}X_1$ or 2-furanyl, where $R_{229}$ is —H or $C_1$-$C_3$ alkyl, where j is 0 through 3 and $X_1$ is as defined above, [D]

(6) 1-piperazinyl substituted in the 4-position with $X_2$—$(CH_2)_j$—, where $X_2$ and j are as defined above, [E]

(7) 1-piperazinyl substituted in the 4-position with $X_1$—$(CH_2)_j$—, where $X_1$ and j are as defined above, [F]

(8) 4-hydroxy-1-piperidinyl substituted in the 4-position with $X_1$ as defined above, [G]

(9) 1-piperazinyl substituted in the 4-position with $X_2$—$NR_{229}$—CO—$(CH_2)_i$—, where $X_2$, $R_{229}$ and i are as defined above; [N]

(D-II) $R_{16}$ is $\alpha$-$R_{163}$:$\beta$-$RI_{164}$ where one of $R_{163}$ and $R_{164}$ is —H and the other is —H, —F, —$CH_3$ or —OH, and $R_{17}$ is —CH—$(CH_2)_p$—$NR_{21}R_{210}$, where p is 1 or 2, where $R_{21}$ and $R_{210}$ are as defined above;

(D-III) $R_{16}$ is $\alpha$-$R_{165}$:$\beta$-$R_{166}$ and $R_{17}$ is $\alpha$-$R_{175}$:$\beta$-$R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2$-$C_7$ alkanoyloxy or —O—CO—$X_1$, where $X_1$ is as defined above, and where $R_{176}$ is —C(=Z)—$(CH_2)_n$—$NR_{21}R_{210}$, where Z, n, $R_{21}$ and $R_{210}$ are as defined above;

(D-IV) the 16, 17-acetonide of a compound where $R_{165}$ is —OH, $R_{166}$ is —H, $R_{175}$ is —OH and $R_{176}$ is —C(=Z)—$(CH_2)_n$—$NR_{21}R_{210}$, where Z, n, —$R_{21}$ and $R_{210}$ are as defined above;

and the pharmaceutically acceptable salts, hydrates and solvates thereof;

with the following overall provisos that:

(I) one of $R_{161}$ or $R_{162}$ is taken together with one of $R_{171}$ or $R_{172}$ to form a second bond between $C_{16}$ and $C_{17}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (II) $R_{17}$ is —CH—$(CH_2)_p$—$NR_{21}R_{210}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (III) $R_5$ and $R_{10}$ taken together are =CH—CH=C($OR_3$)—CH=, only when $R_{17}$ is $\alpha$-$R_{175}$:$\beta$-$R_{176}$ or the 16,17-acetonide of a compound where $R_{16}$ is $\alpha$-OH: $\beta$-H and $R_{17}$ is $\alpha$-OH: $\beta$C(=Z)—$(CH_2)_n$—$NR_{21}R_{210}$, and (IV) $R_5$ is $\alpha$-$R_{57}$:$\beta$-$R_{58}$, only when $R_{17}$ is $\alpha$-$R_{175}$:$\beta$-$R_{176}$ or $\alpha$-OH: $\beta$-C—(=Z)—$(CH_2)_n$—$NR_{21}R_{210}$, or the 16, 17-acetonide thereof;

and an effective stabilizing amount of lightly-cross-linked carboxy-containing polymer, in an aqueous medium.

26. The composition according to claim 25 wherein the therapeutic agent is selected from the group consisting of 21-[4-(2,6-dipyrrolidinyl-4-pyrimidinyl)-1-piperazinyl]-16$\alpha$-methylpregna-1,4,9(11)-triene-3,20-dione or a pharmaceutically acceptable salt, hydrate or solvate thereof; 21-[4-[5,6-bis(diethylamino)-2-pyridinyl]-1-piperazinyl]-16$\alpha$-methylpregna-1,4,9(11)-triene-3,20-dione, or a pharmaceutically acceptable salt, hydrate or solvate thereof; and 21-[4-(3-ethylamino-2-pyridinyl)-1-piperazinyl]-16$\alpha$-methylpregna-1,4,9(11)-triene-3,20-dione, or a pharmaceutically acceptable salt, hydrate or solvate thereof.

27. The composition according to claim 26 wherein the therapeutic agent is selected from the group consisting of the methanesulfonate salt of 21-[4-(2,6-dipyrrolidinyl-4-pyrimidinyl)-1-piperazinyl]-16$\alpha$-methyl-pregna-1,4,9(11)-triene-3,20-dione; 21-[4-[5,6-bis(diethylamino)-2-pyridinyl]-1-piperazinyl]-16$\alpha$-methylpregna-1,4,9(11)-triene-3,20-dione; and 21-[4-(3-ethylamino-2-pyridinyl)-1-piperazinyl]-16$\alpha$-methylpregna-1,4,9(11)-triene-3,20-dione.

28. The composition according to claim 25, wherein the polymer is prepared from at least about 90% by weight, based on the total weight of monomers present, of one or more carboxyl-containing monoethylenically unsaturated monomers.

29. The composition according to claim 25, wherein the monomers are selected from the group consisting of acrylic and methacrylic acid.

30. The composition according to claim 29, wherein the polymer is prepared by cross-linking with less than about 5% by weight, based on the total weight of monomers present, of a polyfunctional cross-linking agent.

31. The composition according to claim 30, wherein the lightly cross-linked carboxy-containing polymer is polycarbophil.

32. The composition according to claim 31, wherein the polycarbophil is a suspension-polymerized acrylic acid and divinyl glycol AA1.

33. The composition according to claim 30 wherein the lightly cross-linked carboxy-containing polymer is a polyalkenyl polyether, lightly crosslinked carboxy-containing polymer.

34. The composition according to claim 30, wherein the polymer is present in an amount of from about 0.1% to about 6.5% by weight, based on the total weight of the composition.

35. The composition according to claim 25, wherein the therapeutic agent is present in an amount of from about 0.01% to about 10% by weight, based on the total weight of the composition.

36. The composition according to claim 35, formulated for topical administration.

* * * * *